United States Patent
Johnson

(10) Patent No.: US 9,416,061 B2
(45) Date of Patent: *Aug. 16, 2016

(54) USE OF SYNERGISTIC MICROORGANISMS AND NUTRIENTS TO PRODUCE SIGNALS THAT FACILITATE THE GERMINATION AND PLANT ROOT COLONIZATION OF MYCORRHIZAL FUNGI IN PHOSPHORUS RICH ENVIRONMENTS

(71) Applicant: Novozymes BioAg A/S, Bagsvaerd (DK)

(72) Inventor: Thomas D. Johnson, Buffalo, SD (US)

(73) Assignee: NOVOZYMES BIOAG A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 14/684,592

(22) Filed: Apr. 13, 2015

(65) Prior Publication Data

US 2015/0329434 A1 Nov. 19, 2015

Related U.S. Application Data

(63) Continuation of application No. 13/815,856, filed on Mar. 15, 2013, now Pat. No. 9,017,442.

(60) Provisional application No. 61/687,210, filed on Apr. 20, 2012.

(51) Int. Cl.
*C05F 11/08* (2006.01)
*C05B 15/00* (2006.01)
(Continued)

(52) U.S. Cl.
CPC ............... *C05F 11/08* (2013.01); *C05B 15/00* (2013.01); *C12N 1/14* (2013.01); *C12N 1/20* (2013.01)

(58) Field of Classification Search
CPC ............. C05F 11/08; C12N 1/14; C12N 1/20; C05B 15/00
See application file for complete search history.

(56) References Cited

U.S. PATENT DOCUMENTS 4,476,881 A 10/1984 Gravely et al.
4,489,161 A 12/1984 Papavizas
(Continued)

FOREIGN PATENT DOCUMENTS

CN 101665374 A 3/2010
WO 2010/008423 A1 7/2010

OTHER PUBLICATIONS

Afek et al. Mycorrhizal species,root age,position of Mycorrhizal inoculum influence colonization of cotton,onion,pepper seedlings. J.Amer.Soc.Hort.Sci. 1990. 938-942. 115(6).

(Continued)

*Primary Examiner* — Jennifer A Smith
(74) *Attorney, Agent, or Firm* — Adam Rucker

(57) ABSTRACT

A composition of matter comprising: a combination of a phytate and a plurality of microorganisms comprising a *Trichoderma virens* fungus, a *Bacillus amyloliquefaciens* bacterium, and one or a plurality of mycorrhizae fungi that is placed in the vicinity of a plant root in a manner that allows the microorganisms in the composition of matter to colonize said plant root; and a method for increasing plant yield comprising: placing a combination of a phytate and a plurality of microorganisms comprising a *Trichoderma virens* fungus, a *Bacillus amyloliquefaciens* bacterium, and one or a plurality of mycorrhizae fungi in the vicinity of a plant root in a manner that allows the microorganisms in the composition of matter to colonize said plant root.

20 Claims, 10 Drawing Sheets

2011 Watertown, SD corn screen trials

| No. | Name | No Starter | Rank | 10-34-0 | Rank |
|---|---|---|---|---|---|
| 1 | CHK | 121.05 g | 7 | 135.37 cde | 4 |
| 2 | Myco IF | 132.72 f | 4 | 133.39 ef | 5 |
| 3 | Myco+T.V.+B.A. IF | 129.22 ef | 6 | 127.77 g | 7 |
| 4 | Phytate IF | 130.96 ef | 5 | 136.24 cde | 3 |
| 5 | Phytate+Myco IF | 137.39 cd | 3 | 132.11 ef | 6 |
| 6 | Phytate+T.V.+B.A. IF | 144.57 ab | 2 | 137.73 bcd | 2 |
| 7 | Phytate+Myco+T.V.+B.A. IF | 147.44 a | 1 | 146.39 a | 1 |
| LSD (P=.10) | | 4.274 | | 3.475 | |
| Standard Deviation | | 4.822 | | 3.921 | |
| CV | | 3.59 | | 2.92 | |

(51) Int. Cl.
*C12N 1/14* (2006.01)
*C12N 1/20* (2006.01)

(56) References Cited

U.S. PATENT DOCUMENTS

| | | |
|---|---|---|
| 4,642,131 A | 2/1987 | Hoitink |
| 4,668,512 A | 5/1987 | Lewis et al. |
| 4,678,669 A | 7/1987 | Ricard |
| 4,713,342 A | 12/1987 | Chet et al. |
| 4,724,147 A | 2/1988 | Marois et al. |
| 4,748,021 A | 5/1988 | Chet et al. |
| 4,818,530 A | 4/1989 | Marois et al. |
| 4,828,600 A | 5/1989 | McCabe et al. |
| 4,877,738 A | 10/1989 | Handelsman et al. |
| 4,915,944 A | 4/1990 | Chet et al. |
| 4,952,229 A | 8/1990 | Muir |
| 5,047,239 A | 9/1991 | Pusey |
| 5,049,379 A | 9/1991 | Handelsman et al. |
| 5,068,105 A | 11/1991 | Lewis et al. |
| 5,071,462 A | 12/1991 | Kimura |
| 5,084,272 A | 1/1992 | Speakman et al. |
| 5,194,258 A | 3/1993 | Paau et al. |
| 5,238,690 A | 8/1993 | Elad et al. |
| 5,260,213 A | 11/1993 | Harman et al. |
| 5,266,316 A | 11/1993 | Elad et al. |
| 5,273,749 A | 12/1993 | Bok et al. |
| 5,300,127 A | 4/1994 | Williams |
| 5,344,647 A | 9/1994 | Rossall |
| 5,401,655 A | 3/1995 | Kijima et al. |
| 5,409,509 A | 4/1995 | Burth et al. |
| 5,422,107 A | 6/1995 | Kubota |
| 5,455,028 A | 10/1995 | O'Donnell |
| 5,552,138 A | 9/1996 | Handelsman et al. |
| 5,589,381 A | 12/1996 | Neyra et al. |
| 5,614,188 A | 3/1997 | Urano et al. |
| 5,628,144 A | 5/1997 | Eastin |
| 5,632,987 A | 5/1997 | Payne et al. |
| 5,645,831 A | 7/1997 | Chilcott et al. |
| 5,665,354 A | 9/1997 | Neyra et al. |
| 5,667,779 A | 9/1997 | Kubo |
| 5,695,982 A | 12/1997 | Handelsman et al. |
| 5,702,701 A | 12/1997 | O'Donnell |
| 5,753,222 A | 5/1998 | Marrone et al. |
| 5,852,054 A | 12/1998 | Handelsman et al. |
| 5,869,042 A | 2/1999 | Marrone et al. |
| 5,882,641 A | 3/1999 | Shetty |
| 5,882,915 A | 3/1999 | Howell |
| 5,906,818 A | 5/1999 | Heins et al. |
| 5,916,029 A | 6/1999 | Smith et al. |
| 5,919,447 A | 7/1999 | Marrone et al. |
| 5,922,603 A | 7/1999 | Herrera-Estrella et al. |
| 5,972,689 A | 10/1999 | Cook et al. |
| 5,974,734 A | 11/1999 | Eastin |
| 5,994,117 A | 11/1999 | Bacon et al. |
| 5,998,196 A | 12/1999 | Handelsman et al. |
| 6,015,553 A | 1/2000 | Germida et al. |
| 6,017,525 A | 1/2000 | Logan et al. |
| 6,030,610 A | 2/2000 | Handelsman et al. |
| 6,033,659 A | 3/2000 | Handelsman et al. |
| 6,060,051 A | 5/2000 | Heins et al. |
| 6,103,228 A | 8/2000 | Heins et al. |
| 6,232,270 B1 | 5/2001 | Branly et al. |
| 6,309,440 B1 | 10/2001 | Yamashita |
| 6,326,016 B2 | 12/2001 | Moesinger |
| 6,385,902 B1 | 5/2002 | Schipper et al. |
| 6,808,917 B1 | 10/2004 | Johnson |
| 6,874,277 B2 | 4/2005 | Yamashita |
| 7,429,477 B2 | 9/2008 | Johnson |
| 8,148,138 B2 | 4/2012 | Johnson |
| 2005/0096225 A1 | 5/2005 | Johnson |
| 2008/0163658 A1 | 7/2008 | Spittle |

OTHER PUBLICATIONS

Artursson et al, 2006, Environ Microbiol 8 (1), 1-10.
Singh et al, 2011, Physiol Mol Biol Plants 17(2), 93-103.

2011 Watertown, SD corn screen trials

| No. | Name | No Starter | | Rank | 10-34-0 | | Rank |
|---|---|---|---|---|---|---|---|
| 1 | CHK | 121.05 | g | 7 | 135.37 | cde | 4 |
| 2 | Myco IF | 132.72 | f | 4 | 133.39 | ef | 5 |
| 3 | Myco+T.V.+B.A. IF | 129.22 | ef | 6 | 127.77 | g | 7 |
| 4 | Phytate IF | 130.96 | ef | 5 | 136.24 | cde | 3 |
| 5 | Phytate+Myco IF | 137.39 | cd | 3 | 132.11 | ef | 6 |
| 6 | Phytate+T.V.+B.A. IF | 144.57 | ab | 2 | 137.73 | bcd | 2 |
| 7 | Phytate+Myco+T.V.+B.A. IF | 147.44 | a | 1 | 146.39 | a | 1 |
| LSD (P=.10) | | 4.274 | | | 3.475 | | |
| Standard Deviation | | 4.822 | | | 3.921 | | |
| CV | | 3.59 | | | 2.92 | | |

FIG. 1

| Trt | Treatment | Plant Height (cm) | | Shoot Mass (g) | | Root Mass (g) | | Length (cm) | | Surface Area (cm2) | | Root Volume (cm3) | | Tips | |
|---|---|---|---|---|---|---|---|---|---|---|---|---|---|---|---|
| 1 | Chk | 62.43 | c | 6.03 | c | 1.44 | b | 2935.07 | a | 340.74 | a | 3.16 | a | 6336.71 | b |
| 2 | Phytate IF | 58.29 | c | 6.17 | c | 1.56 | b | 3124.72 | a | 359.25 | a | 3.31 | a | 6119.57 | b |
| 3 | Phytate + T.V.+B.A. IF | 69.29 | b | 8.56 | b | 1.74 | b | 3245.09 | a | 398.12 | a | 3.95 | a | 7443.14 | b |
| 4 | Phytate + Myco IF | 70.43 | ab | 8.37 | b | 2.01 | b | 3108.2 | a | 411.87 | a | 4.47 | a | 7861.57 | ab |
| 5 | Phytate+Myco+ T.V.+B.A. IF | 76.02 | a | 11.52 | a | 3.09 | a | 3333.75 | a | 450.8 | a | 4.89 | a | 9249.42 | a |
| LSD (P=.05) | | 5.886 | | 1.598 | | 0.917 | | 453.694 | | 84.09 | | 1.306 | | 1711.908 | |
| Standard Deviation | | 5.322 | | 1.445 | | 0.829 | | 410.239 | | 76.035 | | 1.181 | | 1547.939 | |
| CV | | 7.91 | | 17.77 | | 42.09 | | 13.03 | | 19.39 | | 29.86 | | 20.91 | |
| Grand Mean | | 67.29 | | 8.13 | | 1.97 | | 3149.37 | | 392.16 | | 3.96 | | 7402.08 | |
| Bartlett's X2 | | 6.503 | | 5.073 | | 6.26 | | 1.991 | | 4.893 | | 7.69 | | 5.371 | |
| P(Bartlett's X2) | | 0.165 | | 0.28 | | 0.181 | | 0.737 | | 0.298 | | 0.104 | | 0.251 | |
| Friedman's X2 | | 18.286 | | 18.743 | | 11.4 | | 5.6 | | 9.714 | | 8.8 | | 10.171 | |
| P(Friedman's X2) | | 0.001 | | 0.001 | | 0.022 | | 0.231 | | 0.046 | | 0.066 | | 0.038 | |

FIG. 2

Phytic Acid   Myo Inositol triphosphate

3 moles Pi

Cations Release
$K^+$, $Mg^{2+}$, $Zn^{2+}$, $Ca^{2+}$

USE OF SYNERGISTIC MICROORGANISMS AND NUTRIENTS TO PRODUCE SIGNALS THAT FACILITATE THE GERMINATION AND PLANT ROOT COLONIZATION OF MYCORRHIZAL FUNGI IN PHOSPHORUS RICH ENVIRONMENTS

CROSS-REFERENCE TO RELATED APPLICATIONS

This application is a continuation of U.S. application Ser. No. 13/815,856, filed Mar. 15, 2013 (now allowed), which claims the benefit of U.S. provisional patent application No. 61/687,210, filed Apr. 20, 2012, the disclosure of each of which is incorporated by reference as if fully set forth herein.

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC

Not Applicable

BACKGROUND OF THE INVENTION

This invention relates to combining synergistic microorganisms to produce the signals that are necessary to facilitate germination and plant root colonization of mycorrhizae fungi. The colonization of the plant root by mycorrhizal fungi results in the increase of the availability of nutrients to plants, control of pathogens, and improved soil structure and/or soil quality. In particular, an illustrative embodiment of the invention relates to combining phytate as a nutrient source with a combination of *Trichoderma virens*, *Bacillus amyloliquefaciens*, and mycorrhizal fungi, including the following known species: *Glomus intraradices*, *Glomus etunicatum*, *Glomus aggregatum*, *Glomus mosseae*, for the purpose of replacing, duplicating, or enhancing the effect of standard phosphorus-containing fertilizer compounds, such as a 10-34-0, 9-18-9, 3-18-18 fertilizer or other NPK fertilizer combinations.

Phytic acid [known as inositol hexakisphosphate (IP6) or phytate when in salt form] is the principal storage form of phosphorus in many plant tissues, especially bran and seeds. Phytate is also a major form of organic phosphorus within the soil profile, typically constituting 20%-50% of soil organic phosphorus.

*Trichoderma* is a genus of fungi that contains about 20 species. Synonyms for the genus name include *Aleurisma* and *Sporoderma*. *Trichoderma virens*, which is also called *Gliocladium virens*, is a member of the genus. The natural habitats of these fungi include soil and plant material. A member of the genus, *Trichoderma harzianum* KRL-AG2 (ATCC 20847) also known as strain T-22, is used as a biocontrol agent that is applied as a seed or soil treatment or on cuttings and transplants. Strains of the species, *Trichoderma virens*, have also been used for control of damping off diseases in plants. For example, *Trichoderma* (*Gliocladium*) *virens* Gl-21 is known and commercially available at a reasonable price, and is being marketed under the trademark SoilGuard® 12G (EPA Registration Number: 70051-3 and EPA Establishment Number: 067250-IL-001). It is manufactured by Thermo Trilogy Corporation of Columbia, Md. Other known and commercially available *Trichoderma virens* strains include those having the following ATCC accession numbers: 10043, 10044, 10045, 13213, 13362, 204067, 204443, 204444, 204445, 20903, 20904, 20906, 24290, 42955, 44327, 44734, 48179, 52045, 52199, 58676, 58677, 58678, 62399, 64271, 74180, 9645, MYA-297, MYA-298, MYA-649 and MYA-650.

*Bacillus* is a genus of rod-shaped, gram-positive, aerobic or (under some conditions) anaerobic bacteria. *Bacillus* species are widely found in soil and water and some have been used to control plant diseases, including root rot. *Bacillus amyloliquefaciens* is a spore-forming member of the genus. *Bacillus amyloliquefaciens* L.L. Campbell strain F (ATCC 23350) is the type strain for the species. Other known and commercially available *Bacillus amyloliquefaciens* strains include those having the following ATCC accession numbers: 23842, 23843, 23844, 23845, 31592, 49763, 53495 and BAA-390 (Int. J. Sys. Bacteriol. 37:69-71, 1987; J. Bacteriol. 94:1124-1130, 1967).

In the past, before the name was officially changed to recognize that the microorganism was a new species, *Bacillus amyloliquefaciens* was also called *Bacillus subtilis* var. *amyloliquefaciens* by some investigators. A protease produced from *Bacillus subtilis* var. *amyloliquefaciens* is commonly used as a tenderizer for raw meat products. According to the U.S. Environmental Protection Agency (EPA), *Bacillus subtilis* var. *amyloliquefaciens* strain FZB24 is a naturally-occurring microorganism and widespread in the environment. *Bacillus subtilis* var. *amyloliquefaciens* FZB24 (EPA Registration Number: 72098-5 and EPA Establishment Number: 73386-DEU-001) is known and commercially available at a reasonable price, being marketed under the trademark Taegro® by Novozymes, Inc. of Brookfield, Wis.

An arbuscular mycorrhiza fungus is a type of mycorrhiza in which the fungus penetrates the cortical cells of the roots of a vascular plant. Arbuscular mycorrhizae fungi help plants to capture nutrients such as phosphorus, sulfur, nitrogen and micronutrients from the soil. It is believed that the development of the arbuscular mycorrhizal symbiosis played a crucial role in the initial colonization of land by plants and in the evolution of the vascular plants.

The development of arbuscular mycorrhizal fungi prior to root colonization, known as presymbiosis, comprises three stages: propagule germination, hyphal growth, and host recognition and appressorium formation. Propagule are thick-walled multi-nucleate resting structures. Arbuscular mycorrhizal fungi propagules may germinate given suitable conditions of the soil matrix, temperature, carbon dioxide concentration, pH, and phosphorus concentration. The germination of the propagule is not thought to be under direct control of the plant as propagules have been germinated under experimental conditions in the absence of plants both in vitro and in soil. However, the rate of propagule germination can be increased by plant host root exudates.

The growth of arbuscular mycorrhizal hyphae through the soil is controlled by host root exudates and the soil phosphorus concentration. Arbuscular mycorrhizal fungi colonization is higher in nutrient poor soils and decreased with the addition of phosphate fertilizer. Low soil phosphorus concentrations increase hyphal growth and branching as well as induce plant exudation of compounds which control hyphal branching intensity. Arbuscular mycorrhizal fungi also have chemotaxic abilities which enable hyphal growth toward the roots of a potential host plant.

A major challenge for the mycorrhizologist is to understand the extremely harmonious arbuscular mycorrhizal fungus host signaling mechanisms and the colonization process. This harmonious symbiotic relationship is reflected in the obligate biotrophic nature of the fungi, which cannot be cultured in the absence of a host. While success in achieving effective mycorrhizal associations with crop plants growing in sterilized soil has been achieved, the ultimate success for agricultural use of vesicular-arbuscular mycorrhizal (VAM) fungi will occur when they can be used dependably to improve performance of crops grown in nonfumigated soil.

This invention provides a signal that produces propagule germination and subsequent root colonization of mycorrhizae in a very surprising way. It has long been known that seeds store phosphorus as phytate (IP6) and that a germinating seed produces the enzyme phytase to break down the phytate into plant-useable forms to provide nutrients for the seedling. It has also been known that the breakdown of phytate (a six phosphorus molecule) by the enzyme phytase releases three moles of inorganic phosphorus (orthophosphate) and myo-inositol triphosphate (IP3). Plants need phosphorus in an inorganic form, primarily orthophosphate, to take the nutrient into the root. Plants use very little organic phosphorus as they do not possess an effective method to break down phytate. Myo-inositol triphosphate (IP3) is known as a second messenger that can facilitate communications and/or responses between organisms. The release of myo-inositol that occurs through hydrolysis of phytate with *B. amyloliquefaciens* phytase has an impact on plant-microbe interactions and specifically interactions between plants and N fixing bacteria. The signal that is responsible for the germination of mycorrhizae and the subsequent colonization of the plant root by mycorrrhizal fungi is unknown. In addition, the IP3 signal has not been suggested in the literature as having any link to mycorrhizal fungi response, propagule germination, or root colonization. In fact, it is well known that mycorrhizae root colonization can be achieved in low phosphorus soil conditions but it is extremely difficult to produce mycorrhizal germination and root colonization in high phosphorus soil conditions or high phosphorus rhizosphere environment. It is, therefore, also a fact that the literature teaches away from the notion that using a phytase enzyme to reduce phytate and release readily-plant-available phosphorus in the rhizosphere would result in a signal that facilitates germination and subsequent colonization of plant roots by mycorrhizal fungi.

It is likely that additional study of this invention will produce dual and perhaps multiple signal mechanisms as it is known that germination of mycorrhizae propagules can occur in the absence of the plant root; however, the propagule germination is more likely when the root is present. This suggests an unknown signal response.

The background art is characterized by U.S. Pat. Nos. 4,476,881; 4,489,161; 4,642,131; 4,668,512; 4,678,669; 4,713,342; 4,724,147; 4,748,021; 4,818,530; 4,828,600; 4,877,738; 4,915,944; 4,952,229; 5,047,239; 5,049,379; 5,071,462; 5,068,105; 5,084,272; 5,194,258; 5,238,690; 5,260,213; 5,266,316; 5,273,749; 5,300,127; 5,344,647; 5,401,655; 5,422,107; 5,455,028; 5,409,509; 5,552,138; 5,589,381; 5,614,188; 5,628,144; 5,632,987; 5,645,831; 5,665,354; 5,667,779; 5,695,982; 5,702,701; 5,753,222; 5,852,054; 5,869,042; 5,882,641; 5,882,915; 5,906,818; 5,916,029; 5,919,447; 5,922,603; 5,972,689; 5,974,734; 5,994,117; 5,998,196; 6,015,553; 6,017,525; 6,030,610; 6,033,659; 6,060,051; 6,103,228; and 7,339,091; the disclosures of which patents are incorporated by reference as if fully set forth herein.

BRIEF SUMMARY OF THE INVENTION

One aspect of the invention is that it creates an effective association of mycorrhizal fungi with the root of a host plant in a phosphorous rich environment. Other aspects of the invention are the germination of mycorrhizae propagules and subsequent root colonization triggered by a signal molecule. Yet another aspect of the invention is the presence of the IP3 signal molecule. Yet another aspect of the invention is the use of a bacterium that produces a phytase enzyme in a high phosphorous environment because of the presence of the Phy C gene. Yet another aspect of the invention is the use of a microbial component, a *Trichoderma* fungus, that produces phosphatase enzymes that can break the bonds on stable compounds such as tricalium phosphate and release $Ca^{++}$ ions.

As used herein, the following terms and variations thereof have the meanings given below, unless a different meaning is clearly intended by the context in which such term is used:

"A," "an" and "the" and similar referents used herein are to be construed to cover both the singular and the plural unless their usage in context indicates otherwise.

"About" means within one percent of a recited parameter or measurement, and preferably within 0.1 percent of such parameter or measurement.

"Comprise" and variations of the term, such as "comprising" and "comprises," are not intended to exclude other additives, components, integers or steps.

"E" means "times 10 to the power of."

"Exemplary," "illustrative," and "preferred" mean "another."

An illustrative embodiment of the invention comprises a combination of major nutrients, micronutrients, fungi, and bacteria that increases the yield of plants in a manner that is comparable to or superior to the application of a standard fertilizer chemistry.

In use, an illustrative embodiment of the invention creates a synergism that occurs when a proper type and proper ratios of nutrients, fungi, and bacteria are brought together in such a way as to provide plants with available nutrients that increase plant yield or seed yield.

An illustrative embodiment of the invention comprises: a plurality of nutrients, that may or may not be plant-available, combined with a plurality of fungi, and a plurality of bacteria in the presence of a seed, a plant, or a root.

An illustrative embodiment of the invention is a method comprising the following steps: producing a mixture that is comprised of nutrients, fungi, and bacteria in such a way as to produce a synergy between the components; applying the mixture to a seed or applying the mixture in a band in contact with seed or near to the seed or in a soil mixture wherein said fungi and said bacteria reduce said nutrients into a plant-available form, thereby allowing mycorrhizal fungi to colonize the root in the presence of the plant-available nutrients and increasing plant yield or seed yield.

In an illustrative embodiment, the invention is a composition of matter comprising: a combination of phytate and a plurality of microorganisms comprising a *Trichoderma virens* fungus or another calcium solubilizing fungus or a soluble calcium component, a *Bacillus amyloliquefaciens* bacterium or another bacterium that produces a phytase enzyme or a phytase enzyme, and a mycorrhiza fungus or a plurality of mycorrhizae fungi that is placed in the vicinity of a plant root in a manner that allows said plurality of microorganisms in the composition of matter to colonize said plant root.

In another illustrative embodiment, the invention is a method for increasing plant yield comprising: placing a combination of phytate and a plurality of microorganisms comprising a *Trichoderma virens* fungus or another calcium solubilizing fungus or a soluble calcium component, a *Bacillus amyloliquefaciens* bacterium or another bacterium that produces a phytase enzyme or a phytase enzyme and a mycorrhiza fungus or a plurality of mycorrhizae fungi in the vicinity of a plant root in a manner that allows said microorganisms to colonize said plant root. Preferably, said composition is placed in the vicinity of said plant root by application to a preplanted seed, by in-furrow applications as a seed is being planted, or by broadcast over a seed row.

In yet another preferred embodiment, the invention is a method for improving soil aggregation and soil quality by placing a *Trichoderma virens* fungus, a *Bacillus amyloliquefaciens* bacterium or another bacterium that produces a phytase enzyme, and a mycorrhiza fungus or a plurality of mycorrhizae fungi in the vicinity of a plant root in a manner that allows said microorganisms to colonize said plant root.

In another illustrative embodiment, the invention is a composition of matter comprising: about 30,000 propagules of Mycorrhizae in about five gallons of water; about one gallon of an about 15 to about 40 percent aqueous solution of a phytate; about 6.75E8 to about 4.20E9 colony forming units of *Trichoderma virens*; and about 1.35E10 to about 8.40E10 colony forming units *Bacillus amyloliquefaciens*.

In another illustrative embodiment, the invention is a composition of matter comprising: a combination of a phytate and a plurality of microorganisms comprising a *Trichoderma virens* fungus or another calcium solubilizing fungus, a *Bacillus amyloliquefaciens* bacterium or another bacterium that produces a phytase enzyme, and a mycorrhiza fungus or a plurality of mycorrhizae fungi; wherein said combination is operative to enable said plurality of microorganisms to colonize a plant root when said combination is placed in the vicinity of said plant root.

In yet another illustrative embodiment, the invention is a composition of matter comprising: a phytate or phytic acid; means for producing a soluble calcium or a soluble calcium; and means for producing a phytase enzyme or a phytase enzyme.

In a further illustrative embodiment, the invention is a composition of matter comprising: a plurality of nutrients comprising an organic phosphorus (e.g., a phytate or phytic acid), combined with a plurality of fungi, and a plurality of bacteria in the presence of a seed, a plant, or a root.

In another illustrative embodiment, the invention is a composition of matter comprising: a *Trichoderma virens* component; a *Bacillus amyloliquefaciens* component; a mycorrhizal fungus or mycorrhizal fungi component; and a phytate or phytic acid component.

In yet another illustrative embodiment, the invention is a method comprising: producing a mixture that is comprised of a nutrient component, a fungus component, and a bacterium component that is operative to produce a synergy among the components; applying said mixture to a seed or applying said mixture in a growth medium in contact with said seed or near to said seed or in a soil mixture wherein, said fungus component and said bacterium component reduce said nutrient component into a plant-available form; allowing a mycorrhizal fungus to colonize a root produced by said seed in the presence of said plant-available form and increasing plant yield or seed yield.

In a further illustrative embodiment, the invention is a method for increasing plant yield comprising: placing a combination of phytate and a plurality of microorganisms comprising a *Trichoderma virens* fungus or another calcium solubilizing fungal component, a *Bacillus amyloliquefaciens* bacterium or another bacterial phytase enzyme producing bacterial component and a mycorrhiza fungus or a plurality of mycorrhizae fungi in the vicinity of a plant root in a manner that allows said microorganisms to colonize said plant root. In another embodiment, the method further comprises: applying said *Trichoderma virens* fungus or another calcium solubilizing fungal component in a concentration ranging from about 1.0E7 to about 1.0E11 colony forming unit per gram (cfu/g) or colony forming unit per milliliter (cfu/ml) of viable *Trichoderma virens* Gl-3 or *Trichoderma virens* strain Gl-21 spores per gram of said *Trichoderma virens* fungus or another calcium solubilizing fungal component and at an application rate of about 1.35 g per acre or 1.35 ml per acre. In another embodiment, the method further comprises: applying said *Bacillus amyloliquefaciens* bacterium or another phytase enzyme producing bacterial component in a concentration ranging from about 1E7 to about 5E11 cfu/g or cfu/ml of viable *Bacillus amyloliquefaciens* strain BAA-3 or *Bacillus amyloliquefaciens* strain FZB24 spores per gram of *Bacillus amyloliquefaciens* bacterium or another phytase enzyme producing bacterial component and at an application rate of about 1.35 g or 1.35 ml per acre. In another embodiment, said combination is placed in the vicinity of said plant root by application to a pre-planted seed, by in-furrow application as a seed is being planted, or by broadcasting over a seed row.

In a further illustrative embodiment, the invention is a method for improving soil aggregation and soil quality comprising: placing a *Trichoderma virens* fungus or another calcium solubilizing fungus, a *Bacillus amyloliquefaciens* bacterium or another bacterium that produces a phytase enzyme, and a mycorrhiza fungus or a plurality of mycorrhizae fungi in the vicinity of a plant root in a manner that allows said fungi and bacterium to colonize said plant root.

In another illustrative embodiment, the invention is a method for increasing the yield of a plant, said method comprising: using a phytase enzyme to reduce phytate and release readily-plant-available phosphorus in a rhizosphere in which said plant is growing; and producing a signal molecule that facilitates germination of a mycorrhizal fungus and subsequent colonization of the roots of the plant by said mycorrhizal fungus. In another embodiment, said signal molecule is myo-inostitol triphosphate. In another embodiment, the method further comprises: using a *Bacillus amyloliquefaciens* bacterium to produce said phytase enzyme in said rhizosphere. In another embodiment, the method further comprises: using a microorganism to produce said phytase enzyme. In another embodiment, said germination and root colonization occurs in a high phosphorus environment created by applying a fertilizer comprising phosphorus to said rhizosphere. In another embodiment, the method further comprises: using a *Trichoderma* fungus to produce a phosphatase enzyme that is operative to break the bonds on tricalium phosphate and release calcium ions. In another embodiment, the *Trichoderma* fungus is *Trichoderma virens* Gl-3.

In a further illustrative embodiment, the invention is a method for increasing the yield of a crop, said method comprising: applying a composition of matter comprising the following components to each acre of cropland: about one quart of an about 40 percent (by weight) phytate solution; about one gallon to five gallons of water or water plus a standard NPK fertilizer; about 1.35 g of a *B. amyloliquefaciens* TJ1000 spore composition (at a concentration of about 1E10 cfu/g); about 1.35 g of a *T. virens* Gl-3 spore composition (at a concentration of about 5.0E8 cfu/g); and about 0.136 g of a Mycorrhizae propagule composition (at a concentration of about 220,000 propagules/g). In another embodiment, the method further comprises: mixing the composition of matter in a fertilizer applicator tank; and applying it to the cropland in a furrow or a band in close proximity to a seed furrow or a plant root.

In another illustrative embodiment, the invention is a method for increasing the yield of a crop, said method comprising: applying a composition of matter to each acre of cropland; wherein said composition of matter comprises: about 30,000 propagules of Mycorrhizae in about five gallons of water, about one gallon of an about 15 to about 40 percent aqueous solution of a phytate, about 6.75E8 to about 4.20E9 colony forming units of *Trichoderma virens*, and about 1.35E10 to about 8.40E10 colony forming units *Bacillus amyloliquefaciens*.

Further aspects of the invention will become apparent from consideration of the drawings and the ensuing description of exemplary embodiments of the invention. A person skilled in the art will realize that other embodiments of the invention are possible and that the details of the invention can be modified in a number of respects, all without departing from the concept. Thus, the following drawings and description are to be regarded as illustrative in nature and not restrictive.

BRIEF DESCRIPTION OF THE SEVERAL VIEWS OF THE DRAWINGS

The features of the invention will be better understood by reference to the accompanying drawings which illustrate exemplary embodiments of the invention. In the drawings:

FIG. 1 is a table that presents yield data from a field trial of an illustrative embodiment of the invention that was conducted near Watertown, S. Dak. in 2011. The crop grown in the trial was a 95 Relative Maturity hybrid corn. In FIG. 1, CHK stands for Check and represent the untreated control within the trial, Myco stands for mycorrhizal fungi, IF stands for in furrow application, T.V stands for *Trichoderma* vixens, B.A. stands for *Bacillus amyloliquefaciens*, LSD stands for least significant difference and CV stands for coefficient of variation. In the footnotes, "a" denotes the corresponding value is significantly different from any other value that does not contain the letter "a"; "ab" denotes the corresponding value is significantly different from any other value that does not contain the letters "ab"; "bcd" denotes the corresponding value is significantly different from any other value that does not contain the letters "bcd"; "cd" denotes the corresponding value is significantly different from any other value that does not contain the letters "cd"; "ef" denotes the corresponding value is significantly different from any other value that does not contain the letters "ef"; "f" denotes the corresponding value is significantly different from any other value that does not contain the letter "f"; "cde" denotes the corresponding value is significantly different from any other value that does not contain the letters "cde"; "g" denotes the corresponding value is significantly different from any other value that does not contain the letter "g".

FIG. 2 is a table that shows root scan data from a corn trial conducted in a grow room. In the footnotes, a denotes the corresponding value is significantly different from any other value that does not contain the letter "a"; "ab" denotes the corresponding value is significantly different from any other value that does not contain the letters "ab"; "b" denotes the corresponding value is significantly different from any other value that does not contain the letter "b"; "c" denotes the corresponding value is significantly different from any other value that does not contain the letters "c".

DETAILED DESCRIPTION OF THE INVENTION

Figure 3:
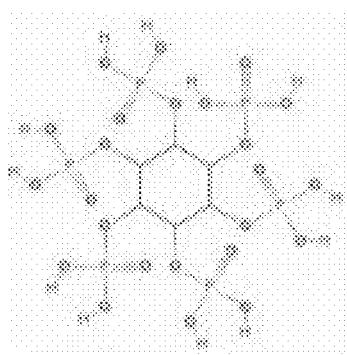
FIG. 3 is a schematic diagram illustrating the *Bacillus amyloliquefaciens* production of the enzyme phytase and the reaction of phytase on phytate (IP6) and the subsequent breakdown into 3 moles of inorganic Phosphorous and the signal component Myo Inositol triphosphate (IP3).
Figure 3:
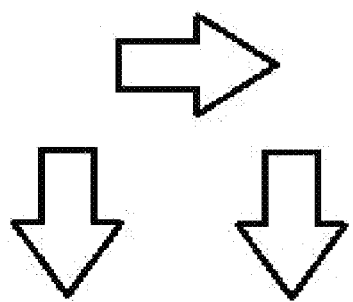
Figure 3:
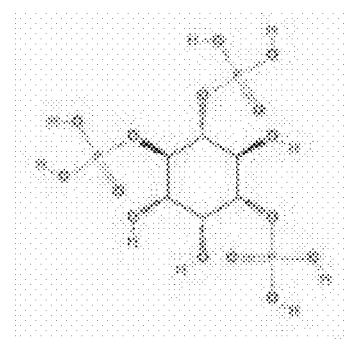

This disclosure incorporates by reference the disclosures of U.S. Pat. Nos. 6,808,917, 7,429,477, and 8,148,138 and U.S. Patent Application Publication No. US 2005-0096225 A1 as if fully set forth herein.

In an illustrative embodiment, the invention comprises four components: a *Trichoderma virens* component, a *Bacillus amyloliquefaciens* component, a mycorrhizal fungi component, and a phytate or phytic acid component.

In an illustrative embodiment of the invention, the *Trichoderma virens* component (e.g., a composition comprising *Trichoderma virens* Gl-3) is grown using solid substrate techniques. The fungal culture is first grown using submerged culture liquid fermentation. The culture is evaluated for contaminants using hemacytometer counts and serial dilution on potato dextrose agar (PDA) and is then incubated at 20 degrees Centigrade (C) for 48 hours and on tryptic soy agar (TSA) and is then incubated at 37 degrees C. for 24 and 48 hours to check for contaminants in the culture. Pure liquid culture is then sprayed evenly on fermentation beds containing a solid substrate (e.g., barley, rice hulls, wheat bran, or an organic nutrient substrate, such as paper pulp supplemented with inorganic nutrient sources). Penicillin is added at this stage to insure that no bacterial contaminants are present. After incubation on the fermentation beds, the culture is evaluated for contaminates using previously described methods, and once the culture is determined not to have contaminants, it is dried to 15 percent moisture by weight. Spores are then separated from the substrate using vibratory separators and evaluated for titer concentration and contamination using serial dilution grown on PDA and TSA as well as hemacytometer counts. The culture is then standardized using dextrose to 1×10e9 colony forming units per gram (cfu/g) and final titer concentration and contaminate evaluation using serial dilution onto PDA is done to confirm product integrity.

The *Trichoderma virens* (e.g., *Trichoderma virens* Gl-3) component of the invention has a preferred application concentration of 5E8 cfu/g (if a liquid suspension, cfu/ml) and is preferably applied at 1.35 g (1.35 ml) per acre. An acceptable concentration range is from 1.0E7 to 1.0E11 cfu/g of viable *Trichoderma virens* Gl-3 spores per gram of *Trichoderma virens* component. In an illustrative embodiment, the percent by weight of this component may range between 1 percent and 99 percent of the total weight of *Trichoderma virens* spores and *Bacillus amyloliquefaciens* spores.

An illustrative embodiment of the invention comprises the fungus *Trichoderma virens* isolate Gl-3 (ATCC 58678) or other isolates. These microorganisms may be obtained from the American Type Culture Collection (ATCC), 10801 University Blvd., Manassas, Va. 20110 and other culture collections or isolated from nature.

Another illustrative embodiment of the invention comprises *Trichoderma* (*Gliocladium*) *virens* isolate Gl-21 which is being marketed under the trademark SoilGuard® 12G by Certis USA L.L.C., 9145 Guilford Road, Suite 175, Columbia, Md. 21046.

In addition to *Trichoderma virens* strain Gl-3 and *Trichoderma virens* strain Gl-21, other strains that may be used to make this invention include the following: *Trichoderma virens* T-1 (ATCC 9645), *Trichoderma virens* NCTC 7057 (ATCC 11043), *Trichoderma virens* NCTC 7056 (ATCC 10044), *Trichoderma virens* NCTC 7055 (ATCC 10045), *Trichoderma virens* 167 (ATCC 13213), *Trichoderma virens* UCLA 230 (ATCC 13362), *Trichoderma virens* 031 (ATCC 20903), *Trichoderma virens* 035 (ATCC 20904), *Trichoderma virens* 035 (ATCC 20904), *Trichoderma virens* 41 (ATCC 20906), *Trichoderma virens* ANA 215 (ATCC 24290), *Trichoderma virens* IFO 8349 (ATCC 44734), *Trichoderma virens* NRRL 1828 (ATCC 44734), *Trichoderma virens* ATCC 48179, *Trichoderma virens* GV-P (ATCC 52045) *Trichoderma virens* 290-4 (ATCC 52199), *Trichoderma virens* s Gl-17 (ATCC 58676), *Trichoderma virens* Gl-9 (ATCC 58677), *Trichoderma virens* TUB F-109 (ATCC 62399), *Trichoderma virens* PREM 47610 (ATCC 64271) *Trichoderma virens* MF5783 (ATCC 74180), *Trichoderma virens* ATCC 204067, *Trichoderma virens* s IBT 7706 (ATCC 20443), *Trichoderma virens* IBT 9354 (ATCC 20444), *Trichoderma virens* s IBT 9355 (ATCC 204445), *Trichoderma virens* G-4 (MYA-297), *Trichoderma virens* G-6 (MYA-298), and *Trichoderma virens* GJS 95-194 (MYA-1298).

Because *Trichoderma virens* is widespread in the soil environment, new strains may be isolated in the future and used in other embodiments of the invention. *Trichoderma virens* may be isolated by sampling soil or plant tissue and utilizing serial dilutions to plate out samples onto PDA plates plus penicillin (to reduce bacterial contamination). The colonies are then further isolated. Identity confirmation is performed through DNA sequencing. Other *Trichoderma* species that have similar characteristics to *T. virens* and that may be used in the invention include *T. viride, T. harzanium, T. asperellum* and *T. gamsii* and others. Additionally, since the calcium ion is vital to the stabilization of *B. amyloliquefaciens* phytase, an alternative embodiment involves adding a soluble calcium component or another calcium solubilizing fungus to the soil. Alternatively, any fungus that releases free calcium through a novel enzymatic process that does not require acidification of the calcium molecule may be used. Calcium-solubilizing fungi may be obtained through culture collections (i.e. ATCC; NRRL). Species known to be tri-calcium phosphate solubilizers include *T. virens, T. viride*, and *T. harzanium*. A soluble form of calcium may be obtained from a number of agricultural fertilizer dealers in forms such as calcium sulfate or calcium EDTA. In addition, granular calcium (99.0%) may be obtained from chemical suppliers including Sigma-Aldrich.

In an illustrative embodiment of the invention, the *Bacillus amyloliquefaciens* component (e.g., *Bacillus amyloliquefaciens* TJ-1000) is grown using submerged culture liquid fermentation. The cultures are quality control tested for contamination using serial dilution to 10E12 and grown on PDA and TSA plates. The plates are incubated at 37 degrees C. and evaluated for contamination at 24 and 48 hours. If plate inspection does not reveal any contamination, the culture is then concentrated to remove most of the spent fermentation media. The remaining pellets are then lyophilized. After lyophilization, titer concentration is determined by suspending 10 grams of lyophilized spore powder into 90 ml sterile water containing a surfactant. Serial dilution is used to determine titer concentration of the viable spores and to check for contamination. The culture is then blended with dextrose to standardize the spore powder to 1.0E11 cfu/g.

A preferred application rate for the *Bacillus amyloliquefaciens* component is a solid application rate of 1.35 g per acre at a concentration of 1E10 cfu/g of *Bacillus amyloliquefaciens* or a liquid application rate of 1.35 ml per acre at a concentration of 1E10 cfu/ml. The concentration range may vary from 1E7 cfu/g to 5E11 cfu/g. In an illustrative embodiment, the percentage by weight of this component ranges from 1 percent to 99 percent of the total weight of *Trichoderma virens* spores and *Bacillus amyloliquefaciens* spores.

A further illustrative embodiment of the invention comprises the bacterium *Bacillus amyloliquefaciens* TJ1000 or 1BE. This microorganism was deposited with the ATTC on Oct. 31, 2001, and was assigned accession number ATCC BAA-390. Alternative embodiments of the invention comprise other *Bacillus amyloliquefaciens* strains which may be isolated from nature or obtained from ATCC or other culture collections.

Another illustrative embodiment of the invention comprises *Bacillus amyloliquefaciens* strain FZB24 which is marketed under the trademark Taegro® by Earth Bioscience, Inc., 26 Sherman Court, PO Box 764, Fairfield, Conn. 06430.

Other *Bacillus amyloliquefaciens* strains that may be used to make the invention include *B. amyloliquefaciens* B-543 (NRRL), *B. amyloliquefaciens* B-644 (NRRL), *B. amyloliquefaciens* B-645 (NRRL), *B. amyloliquefaciens* B-942 (NRRL), *B. amyloliquefaciens* NRS-763 (NRRL), *B. amyloliquefaciens* IFO 15535 (ATTC 23350), *B. amyloliquefaciens* T (ATCC 23842), *B. amyloliquefaciens* SB-1 (ATCC 23844), *B. amyloliquefaciens* P (ATCC 23844), *B. amyloliquefaciens* N (ATCC 23845), *B. amyloliquefaciens* K49 (ATCC 27505), *B. amyloliquefaciens* RUB 500H (ATCC 31592), *B. amyloliquefaciens* RUB 500 (ATCC 49763), *B. amyloliquefaciens* H (ATCC 53495), and *B. amyloliquefaciens* 3002 (ATCC 700385). *B. amyloliquefaciens* is a naturally occurring soil/plant bacteria and future strains may be isolated or redesignated as *B. amyloliquefaciens* and used to make the invention. *B. amyloliquefaciens* may be obtained from soil, plant tissue and silage and isolated using serial dilutions and may be classified using DNA sequencing (16S RNA).

Furthermore, in an alternative embodiment, the phyC gene which produces the stable, calcium-dependent phytase enzyme may be produced by another bacterium that is genetically engineered to produce the enzyme, for example, see U.S. Pat. No. 7,339,091 which is incorporated by reference as if fully set forth herein. For this reason, the applicant believes that any bacterium that expresses the phyC gene may be used in the invention to encourage mycorrhizal colonization. The transfer of a gene to another organism can be accomplished by purifying the DNA of a *Bacillus amyloliquefaciens*, designing primers corresponding to the phyC gene sequence, and amplifying the sequence through Polymerase Chain Reaction (PCR). The amplified fragments can then be purified and transferred to another organism by use of a cloning vector. Confirmation that the gene has been inserted by PCR amplification may be accomplished by means of hybridization utilizing the primers used for the initial PCR amplification. A bacterium producing a phytase enzyme may be obtained through culture collections (i.e., ATTC, NRRL). Species known to be phytase producers include *B. amyloliquefaciens* and *B. subtilis*. A phytase enzyme may also be obtained through commercial chemical suppliers such as Sigma-Aldrich. Additionally, many phytase enzymes are used as feed additives for swine and chickens. One such phytase enzymes is Ronozyme®, a product of DSM.

In another alternative embodiment, *B. amyloliquefaciens* is grown in a broth and the phytase produced is combined with Mycorrhizae, *T. virens*, and phytate, thereby producing a combination having the same effect as incorporation of a *Bacillus amyloliquefaciens* bacterium in the invention. For the production of the phytase enzyme, a simple growth media (e.g., a glucose media) is supplemented with phytate and calcium. A *B. amyloliquefaciens* or a genetically modified organism containing the phyC gene is inoculated into the growth media. The phytase enzyme is produced in adequate quantities due to the availability of phytate and calcium. The vegetative cells are removed from the media through a process of centrifugation and the phytase growth media is used to produce an illustrative embodiment of the invention.

The mycorrhizal fungi component of the invention may be cultivated through the following steps. Corn seeds are surface sterilized (most crop seeds may be used but fibrous root crops tend to produce more hyphal branching) and pre-germinated on germination paper. A low phosphorus medium for growing corn plants is sterilized and propagule inoculums of *G. intraradices*, *G. etunicatum*, *G. aggregatum*, and *G. mossae* are obtained from a culture collection. In this embodiment, four separate batches of medium containing one part by volume mycorrhizal inoculums to 20 parts by volume of growing medium are prepared (one batch for each *Glomus* species). The inoculated media are added to 6-10 inch pots. Four to six corn seedlings are planted per pot and allowed growth for 14-16 weeks. The plants are watered daily and are fertilized every week with a low phosphorus fertilizer.

The plants are harvested by removing the roots from the pots and cutting them into small fragments of 1 cm to 2 cm in length. The root fragments from the four *Glomus* species are then preferably mixed together and are used as the mycorrhizal fungi component of the invention. The preferred application rate of the four *Glomus* species is 30,000 total propagules per acre (or 0.136 g at 220,000 propagules/gram). The range of propagules per gram may vary from 50 propagules to 220,000 propagules per gram. This component preferably comprises one percent to 99 percent of the weight of the other biological components of the invention Another illustrative embodiment of the invention comprises a mycorrhizal fungi component which is marketed under the trademark MycoApply® by Mycorrhizal Applications Inc., 810 NW E St., Grants Pass, Oreg. 97526.

In addition to *Glomus intraradices*, *Glomus etunicatum*, *Glomus aggregatum*, and *Glomus mossae*, other *Glomus* species may be used to make mycorrhizal fungi component of the invention, including the following: *G. albidum*, *G. caledonium*, *C. claroideum*, *G. clarum*, *G. clavispora*, *G. constrictum*, *G. coronatum*, *G. deserticola*, *G. diaphanum*, *G. eburneum*, *G. fragilistratum*, *G. gerosporum*, *G. globiferum*, *G. hadleyi*, *G. hyalinum*, *G. insculptum*, *G. lamellosum*, *G. luteum*, *G. macrocarpum*, *G. manihot*, *G. microaggregatum*, *G. mirificum*, *G. monosporum*, *G. pustulatum*, *G. sinuosum*, *G. spurucum*, *G. tortuosum*, *G. verruculosum*, *G. versiforme*, and *G. viscosum* (available from INVAM-West Virginia University). The following endomycorrhizal species may also be used to make the mycorrhizal fungi component of the invention: Ambisporaceae spp.; Archaeosporaceae spp. [*Ar. leptoticha*, *Ar. gerdemannii*, and *A. trappei* (available from INVAM-West Virginia University)] Geosiphonaceae spp., Acaulosporaceae spp. [*A. colossica*, *A. delicatta*, *A. denticulate*, *A. foveata*, *A. koskei*, *A. lacunosa*, *A. laevis*, *A. longula*, *A. mellea*, *A. morrowiae*, *A. rehmii*, *A. scrobiculata*, *A. spinosa*, and *A. tuberculata* (available from INVAM-West Virginia University)]; Enterophosporaceae spp. (*E. colombiana*, *E. contigua*, *E. infrequens*, *E. kentinesis*), Dicersisporaeceae spp, Gigasporaceae spp. [including *Gi. albida*, *Gi. decipiens*, *Gi. gigantea*, *Gi. margarita*, and *Gi. rosea*) (available from INVAM, West Virginia University)]; Paraglomus spp. (*P. brasilianum* and *P. occultum* (available from INVAM-West Virginia University)]; and *Scutellospora* spp (*S. calospora*, *S. cerradensis*, *S. coralloidea*, *S. dipurpurascens*, *S. erythropa*, *S. fulgida*, *S. gregaria*, *S. heterogama*, *S. pellucida*, *S. persica*, *S. reticulate*, *S. rubra*, *S. scutata*, and *S. verruscosa* (available from INVAM-West Virginia University)]. Arbuscular mycorrhizal fungi are naturally occurring soil fungi, and new strains and species may be discovered in the future and used to make the invention.

Another illustrative embodiment of the invention comprises a phytate or phytic acid component which may be obtained from Northwest Scientific, Inc., PO Box 1811 Billings, Mont. 59103. The preferred application rate of phytate is one quart per acre of a 40 percent phytate solution. Because high amounts of phytate do not inhibit mycorrhizal or plant growth, higher application rates may be used. The concentration of phytate in solution may range from one percent to 99 percent weight of phytate as a percentage of the weight of the solution or standard fertilizer chemistry, e.g., a solution containing 9-18-9 or 10-34-0 Nitrogen (N)-Phosphorus (P)-Potassium (K). Thus, water or a solution having a standard fertilizer chemistry, i.e., 10N-34P-0K may be used as the delivery liquid for the phytate/biological composition. Phytate is usually a byproduct of agricultural crop processing or a byproduct of manure treatment/bioreactor facilities. Thus, phytate/phytic acid may be obtained from corn, soybeans, wheat, rice, manure, etc.

In an illustrative embodiment, the invention is a composition of matter comprising: a combination of phytate and a plurality of microorganisms comprising a *Trichoderma virens* fungus, a *Bacillus amyloliquefaciens* bacterium, and one mycorrhiza fungus or a plurality of mycorrhizae fungi that is placed in the vicinity of a plant root in a manner that allows said plurality of microorganisms in the composition of matter to colonize said plant root.

In another embodiment, the invention is a method for increasing plant yield comprising: placing a combination of phytate and a plurality of microorganisms comprising a *Trichoderma virens* fungus, a *Bacillus amyloliquefaciens* bacterium, and a plurality of mycorrhizae fungi in the vicinity of a plant root in a manner that allows said microorganisms to colonize said plant root. In another embodiment, said composition is placed in the vicinity of said plant root by application to a preplanted seed, by in-furrow application as a seed is being planted, or by broadcast over a seed row.

In an illustrative embodiment, the invention is a method comprising applying the following composition of matter to each acre of cropland: about one quart of an about 40 percent (by weight) phytate solution; about one gallon to five gallons of water or water plus a standard NPK fertilizer; 1.35 g of a *B. amyloliquefaciens* TJ1000 spore composition (at a concentration of about 1E10 cfu/g); 1.35 g of a T. vixens Gl-3 spore composition (at a concentration of about 5.0E8 cfu/g); and 0.136 g of a Mycorrhizae propagule composition (at a concentration of about 220,000 propagules/g). The biological components are preferably mixed in a fertilizer applicator tank and applied in furrow or banded in close proximity to the seed furrow or plant root.

Regarding the *Bacillus amyloliquefaciens* component of the invention, a preferred dry, lyophilized formulation has a spore count of about 1E10 cfu/g of *Bacillus amyloliquefaciens* TJ1000 spores and is applied at a preferred rate of 1.35 grams of *Bacillus amyloliquefaciens* component per acre. A preferred liquid application rate is about 1.35 ml of *Bacillus amyloliquefaciens* component per acre at a concentration of about 1E10 cfu/ml of *Bacillus amyloliquefaciens* TJ1000 spores. An acceptable concentration range for the solid formulation is from about 1E7 cfu/g to about 5E11 cfu/g. In a preferred embodiment of the invention, the *Bacillus amyloliquefaciens* component comprises between about one percent to about 99 percent of the combined weight of combined weight of the *Trichoderma virens* component and the *Bacillus amyloliquefaciens* component. These values also be used with other *Bacillus amyloliquefaciens* strains.

With respect to the *Trichoderma virens* component of the invention, the preferred application rate for this component of the invention is about 1.35 gram per acre at a concentration of about 5E8 cfu/gram, with a preferred concentration range of from about 1E7 cfu to about 1E11 cfu of viable *Trichoderma virens* Gl-3 spores per gram of *Trichoderma virens* component. This component as a percent by weight may vary between about one percent to about 99 of the combined weight of the *Trichoderma virens* component and the *Bacillus amyloliquefaciens* component. These values may also be used with other *Trichoderma virens* strains.

With respect to the mycorrhizae fungi component of the invention, the preferred application rate of the four *Glomus* species is about 30,000 propagules per acre (about 0.136 gram of the mycorrhizae fungi component at a concentration of about 220,000 propagules/gram). The range of propagules per gram may vary from about 50 propagules per gram to about 220,000 propagules per gram. This component preferably comprises from about one percent to about 99 percent of the combined weight of the *Trichoderma virens* component and the *Bacillus amyloliquefaciens* component.

With respect to the phytate component of the invention, a preferred application rate of phytate is about one quart per acre of an about 40 percent phytate solution. Because high amounts of phytate will not inhibit mycorrhizal or plant growth, a larger amount may be used. The concentration of the solution may range from one percent to 99 percent w/w phytate/water or a NPK fertilizer solution. Conventional farming practices have been making use of NPK starter or pop up fertilizers which are applied either banded or in furrow at the time of planting. The components in this invention can be applied by themselves, or mixed with water or with NPK fertilizers.

WORKING EXAMPLES

In the working examples, the four Mycorrhizae are *Glomus aggregatum*, *Glomus etunicatum*, *Glomus intraradices*, and *Glomus mossae*. The *Bacillus amyloliquefaciens* strain is *Bacillus amyloliquefaciens* TJ-1000 and the *Trichoderma virens* strain is *Trichoderma virens* Gl-3. As was noted above, other Mycorrhizae species or strains and other *Trichoderma virens* strains and other *Bacillus amyloliquefaciens* strains may be used in practicing the invention.

Referring to FIG. 1, the results of South Dakota (SD) corn field trial are presented. In this field trial, corn was planted in two blocks: one block with no fertilizer applied at planting and the other block had 4 gallons of an industry standard liquid phosphorus fertilizer with an analysis of 10 percent nitrogen and 34 percent phosphorus. The treatments within the blocks were identical and are as follows:

Treatment 1—CHK: This was the untreated check that consisted of corn seed that was treated with the industry standard fungicide/insecticide seed treatment. This seed treatment was consistent throughout the other treatments and blocks.

Treatment 2—Myco IF: This treatment was an in-furrow application of mycorrhizae propagule applied at a rate of 30,000 propagules per acre with 5 gallons of water per acre as a carrier.

Treatment 3—Myco+T.V.+B.A.IF: This treatment was an in-furrow application of Mycorrhizae propagules applied at a rate of 30,000 propagules per acre plus *Trichoderma virens* spore applied at a rate of 4.05E08 per acre and a *Bacillus amyloliquefaciens* spore applied at a rate of 1.35E10 per acre.

Treatment 4—Phytate IF: This treatment was an in-furrow application of a 15 percent phytate solution applied at 1 gallon per acre plus 4 gallons of water for carrier in the No Starter Block or 4 gallons of liquid fertilizer for the 10-34-0 Block.

Treatment 5—Phytate+Myco IF: This treatment was an in-furrow application of Mycorrhizae propagules at a rate of 30,000 propagules per acre in a solution of 15 percent phytate applied at a rate of 1 gallon per acre plus 4 gallons of water for carrier in the No Starter Block or 4 gallons of liquid fertilizer for the 10-34-0 Block.

Treatment 6—Phytate+T.V.+B.A. IF: This treatment was an in-furrow application of a combination of *Trichoderma virens* spore applied at a rate of 4.05E08 per acre and *Bacillus amyloliquefaciens* applied at a rate of 1.35E10 per acre in a 15 percent solution of phytate at a rate of 1 gallon per acre plus 4 gallons of water for carrier in the No Starter Block or 4 gallons of liquid fertilizer for the 10-34-0 Block.

Treatment 7—Phytate+Myco+T.V.+B.A. IF: This treatment was an in-furrow application of a combination of Mycorrhizae propagules at a rate of 30,000 per acre plus *Trichoderma virens* at a rate of 4.05E08 per acre plus *Bacillus amyloliquefaciens* applied at a rate of 1.35E10 per acre in a 15 percent solution of phytate at a rate of 1 gallon per acre plus 4 gallons of water for a carrier in the No Starter Block or 4 gallons of liquid fertilizer for the 10-34-0 block.

Trial Conclusion: The application of Mycorrhizae propagules alone (Treatment 2) produced a significant increase in yield in the No Starter Block but produced no significant yield in the high phosphorus environment in the 10-34-0 Block over the CHK (Treatment 1). This was an expected response as it was expected that Mycorrhizae would experience difficulty producing a yield response in a high phosphorus environment.

When mycorrhizae, *Trichoderma virens*, and *Bacillus amyloliquefaciens* were applied together (Treatment 3) or when phytate was added by itself (Treatment 4) there was no significant yield increase from Treatment 2 in either the No Starter or the 10-34-0 Blocks.

Phytate plus Mycorrhizae (Treatment 5) significantly increased yield when compared to mycorrhizae alone (Treatment 2) in the No Starter Block but did not significantly impact yield in the 10-34-0 Block in that high phosphorus environment.

*Trichoderma virens* and *Bacillus amyloliquefaciens* plus phytate (Treatment 6) significantly increased yield performance over phytate alone (Treatment 4) in the No Starter Block but did not increase the yield in the 10-34-0 Block.

Mycorrhizae, *Trichoderma virens, Bacillus amyloliquefaciens*, plus phytate (Treatment 7) significantly increased yield over all of the other treatment entries (Treatments 1 through 6) in both the No Starter Block and the 10-34-0 Block with the high phosphorus environment. This result was indeed a surprising breakthrough and a confirmation that Treatment 7 is both novel and surprising.

In summary, the data in FIG. 1 show that a mycorrhizal fungi composition (Treatment 2) applied in the seed furrow increased yield in low phosphorus conditions. However, when a mycorrhizal fungi composition was applied in the same manner in high phosphorus conditions (i.e., with four gallons of a 10-34-0 fertilizer) there was no yield response. This is an expected response.

When phytate was applied in combination with a mycorrhizal fungi combination plus a *Trichoderma virens* fungus plus a *Bacillus amyloliquefaciens* bacterium with no starter fertilizer (Treatment 7), corn yield was increased to levels greater than the application of a 10-34-0 fertilizer alone. In addition, the same combination increased corn yield to greater levels even under high phosphorus conditions and was the only treatment that produced significant yield response with the application of a 10-34-0 fertilizer. Both of the results produced by this treatment are surprising. It is well know that mycorrhizal fungi are inhibited from germinating and colonizing the roots of plants in high phosphorus environments or in the presence of an applied phosphorus fertilizer, such as a 10-34-0 fertilizer.

Treatment 7 combined a *Trichoderma virens* fungus and *Bacillus amyloliquefaciens* bacterium with phytate (IP6) and a mychorrizal fungi composition to produce composition that is surprisingly effective at increasing corn yield. The fact that this composition increased yield more effectively that a 10-34-0 fertilizer establishes that a long-sought-after solution for increasing plant yield was discovered by the applicant. The invention allows replacement of a standard chemical fertilizer with one that is microbial in its mode of action. Treatment 7 also provided a mechanism to establish mycorrhizae fungi on the roots of plants in the presence of phosphorus.

Referring to FIG. 2, the results of a corn grow room experiment are presented. Corn was planted in Deepots™ planting cones in a 2:1 sand:soil mixture and randomly replicated within the trays. The treatments were placed 1 inch to the side and 1 inch below where the seeds were planted. The plants were grown under 1000 W dual High Pressure Sodium and Metal Halide lights with a 12 hours on/12 hours off growth cycle. Plants were watered daily with the equivalent of 1 inch water. Corn plants were harvested 28 days after planting.

Treatment 1—Check: The CHK treatment was fungicide seed treatment (FST) and insecticide seed treatment (IST) and this seed treatment was consistent across the trial. The equivalent of 5 gallons of water was placed 1 inch to the side and 1 inch below the seed.

Treatment 2—Phytate: The equivalent of 15 percent phytate at a rate of 1 gallon per acre and water at a rate of 4 gallons per acre were placed 1 inch to the side and 1 inch below the seed.

Treatment 3—Phytate+T.V.+B.A.: The equivalent of *Trichoderma virens* spores at 4.05E08 per acre plus *Bacillus amyloliquefaciens* spores at 1.35E10 per acre plus 15 percent phytate at a rate of 1 gallon per acre and water at 4 gallons per acre.

Treatment 3—Phytate+T.V.+B.A.: The equivalent of *Trichoderma virens* spores at 4.05E08 per acre plus *Bacillus amyloliquefaciens* spores at 1.35E10 per acre plus 15 percent phytate at a rate of 1 gallon per acre and water at 4 gallons per acre.

Treatment 4—Phytate+Myco: The equivalent of Mycorrizhae propagules at 30,000 per acre plus 15 percent phytate at a rate of 1 gallon per acre and water at 4 gallons per acre.

Treatment 5—Phytate+Myco+T.V.+B.A.: The equivalent of Mycorrhizae propagules at 30,000 per acre plus *Trichoderma virens* spores at 4.05E8 per acre plus *Bacillus amyloliquefaciens* spores at 1.35E10 per acre plus 15 percent phytate at 1 gallon per acre and water at a rate of 4 gallons per acre.

The addition of phytate alone (Treatment 2) caused an anti-nutrient property, decreasing plant growth. The addition of phytate+T.V.+B.A. (Treatment 3) and phytate+Myco (Treatment 4) brought increased plant growth. Phytate+Myco+T.V.+B.A. (Treatment 5) brought the greatest yield to plant growth, and this provides evidence that the addition of phytate, *Trichoderma virens* and *Bacillus amyloliquefaciens* can speed up the germination and colonization of Mycorrhizae propagules over a control and over what mycorrhizae can do alone. This trial is further confirmation of the field results presented in FIG. 1.

In summary, in the grow room trial (FIG. 2), plant height, shoot mass, and root mass of Treatment 5 were all significantly different from the control treatment 1. Treatment 5 contains all of the components (phytate, *T. virens, B. amyloliquefaciens*, and mycorrhizae fungi) that produce surprising results. This trial repeats the response of the field trial to further substantiate the surprising results.

FIG. 3 represents the reaction of *Bacillus amyloliquefaciens* production of phytase enzyme and the impact of the of the phytase enzyme on phytate (IP6). This reaction results in the release of 3 moles of inorganic phosphorus plus Myo Inositol Triphosphate (IP3). Myo Inositol Triphosphate is likely acting as a signal to promote the germination and/or root colonization of mychorrhizae.

Use of illustrative embodiments of this invention is advantageous for the growing of most agriculturally important crops. Conventional farming (high phosphorus fertilizer applications, crop rotation, no crop in the ground for extended periods of time, chemical/biological fungicides) reduces native mycorrhizal populations. Increasing the germination and colonization of mycorrhizal fungi allows farmers to reduce input costs and obtain greater yields by utilizing nutrients already present in the soil while still maintaining adequate inorganic nutrient fertilization. Arbuscular mycorrhizal fungi colonize 80 percent of plants—mostly green, leafy plants and commercially produced plants. This invention finds utility in the growing of agriculturally important crops including alfalfa, barley, beans (all), corn, cotton, millet, rice, sorghum, soybeans, sunflower, and wheat. This invention is also applicable to a host of other commercially important crops including but not limited to: acacia, agapanthus, alder, almond, apple, apricot, artichoke, ash, asparagus, aspen, avocado, bamboo, banana, basil, bayberry, beech, begonia, black cherry, blackberry, black locust, blue gramma, box elder, boxwood, buckeye, cacao, cactus, *camellia*, carrisa, carrot, cassava, ceanothus, cedar, celery, cherry, *chrysanthemum*, citrus (all), clover, coconut, coffee, coral tree, cottonwood, cowpea, crab tree, creosote, crytomeria, cucumber, currant, cypress, dogwood, eggplant, elm, *eucalyptus*, euonymus, fern, fescue, fig, flax, flowers (mostly all), forsythia, fuchsia, *gardenia* garlic, geranium, grape (all), grasses (perennials), green ash, guayule, gum, hackberry, hawthorn, hemp, herbs (all), hibiscus, holly, hostas, *impatiens*, jatropha, jojoba, juniper, kiwi, leek, lettuce, *ligustrum*, lily, locust, lychee, mahogany, *magnolia, mahonia*, mango, maples (all), marigolds, mesquite, *mimosa*, morning glory, mulberry, myrtle, nasturtium, okra, olive, onion, pacific yew, palms (all), pampas grass, passion fruit, *papaya*, paw paw, peas, peaches, peanuts, pear, peppers (all), pistachio, persimmon, *pittosporum*, plum, podocarpus, poinsettia, poplar, potato, pumpkin, raspberry, redwood, rice, rose, rubber, ryegrass, sagebrush, saltbrush, serviceberry, *sequoia*, shallot, snapdragon, sourwood, squash, star fruit, strawberry, succulents, sudan grass, sugar cane, sumac, sweet gum, sweet potato, sycamore, *taxus*, tea, tobacco, tomato, violets, yams, *yucca*, and willow.

Most modern planters have a fertilizer/insecticide applicator tank. In illustrative embodiments of this invention, the phytate/microorganisms solution is mixed with water and/or NPK fertilizer and applied either in a band or in furrow application. The solution may also be broadcast applied through a sprayer either prior to or right after seed planting. Phytate may also be applied as a dry powder, prilled, or coated onto a prill with the Mycorrhizae, *B. amyloliquefaciens*, and *T. virens*. It may be applied as a band, in furrow, or broadcast in a field. The combination may also be applied to or mixed in soil and used in greenhouses. The combination may be applied as a seed treatment where components are applied either as a dry treatment to the seed or applied in a liquid solution to the seed.

In another illustrative embodiment, the invention involves combining phytate or phytic acid (Component D) with three microorganisms at a range of possible cfu/g values. Three microorganisms make up three components of the invention: Component A, Component B, and Component C.

In this embodiment, Component A is a composition comprising a *Trichoderma virens* fungus. This component preferably has a viable *Trichoderma virens* concentration range of between about 1.0E6 to about 1.0E11 cfu per gram of Component A. In a preferred embodiment of the invention, Component A preferably comprises between about one percent to about 99 percent of the combined weight of Component A plus Component B (termed Combination AB). A preferred application rate of Component A is about 1.35 gram (at a concentration of about 5.0E8 cfu/gram) per acre of cropland, wherein Component A comprises about 50 percent of the weight of Combination AB.

In this embodiment, Component B is a composition comprising a *Bacillus amyloliquefaciens* bacterium. This component preferably has a viable *Bacillus amyloliquefaciens* concentration range of between about 1.0E7 to about 5.0E11 cfu/gram of Component B. In a preferred embodiment of the invention, Component B preferably comprises between about one percent to about 99 percent of the combined weight of Combination AB. A preferred application rate of Component B is about 1.35 gram (at a concentration of about 1.0E10 cfu/gram) per acre of cropland, wherein Component B comprises about 50 percent of the weight of Combination AB.

In this embodiment, Component C is a composition comprising *Glomus* spp. This component preferably has a viable *Glomus* spp. Concentration range of between about 5000 to about 220,000 propagules/gram. Component C preferably comprises between about one percent to about 99 percent of the combined weight of Combination AB. For example, the biological part of an illustrative embodiment of the invention comprises about 98 percent by weight of Combination AB and about 2 percent by weight of Component C. A preferred application rate of Component C is about 0.136 gram (at a concentration of about 220,000 propagules/gram) or about 30,000 propagules per acre of cropland.

While there is a preferred lower limit of the *Glomus* propagules application rate (e.g., 5,000 propagules per acre of cropland), there is (other than economics) no upper limit to *Glomus* propagule application per acre of cropland. The following chart describes a preferred minimum and maximum ratios of *Bacillus amyloliquefaciens* cfu and *Trichoderma vixens* cfu to *Glomus* propagules.

| | Bacillus amyloliquefaciens minimum | Bacillus amyloliquefaciens Maximum | Trichoderma virens minimum | Trichoderma virens maximum |
|---|---|---|---|---|
| Per each Glomus propagule | 3.3E2 cfu | 1.7E7 cfu | 3.3E1 cfu | 3.3E6 cfu |

The chart above shows the lower and upper limits of what the applicant believes is a range of the effective numbers of *Bacillus* spores and *Trichoderma* spores per each *Glomus* propagule. The upper end of the range is believed to be appropriate for field (crop land) environments but lower rates may be effective in more controlled environments, e.g., in greenhouse settings.

In this embodiment, Component D is a composition comprising phytate. A preferred application rate for Component D is about one quart of an about 40 percent phytate solution per acre. The solution may be with either water or water plus a standard fertilizer (Nitrogen (N), Phosphorus (P), Potassium (K) (for example, a 10-34-0 fertilizer). The phytate concentration may range from about 1 percent to about 90 percent of the weight of the total solution. Alternatively, the phytate component may also be applied in salt form, i.e., as a 99 percent calcium phytate molecule.

Referring to FIG. 3, a schematic diagram illustrating the *Bacillus amyloliquefaciens* reaction is presented. This figure illustrates that using a phytase enzyme to reduce phytate and release readily-plant-available phosphorus in the rhizosphere results in a signal that facilitates germination and subsequent colonization of plant roots by mycorrhizal fungi.

Figure 4:
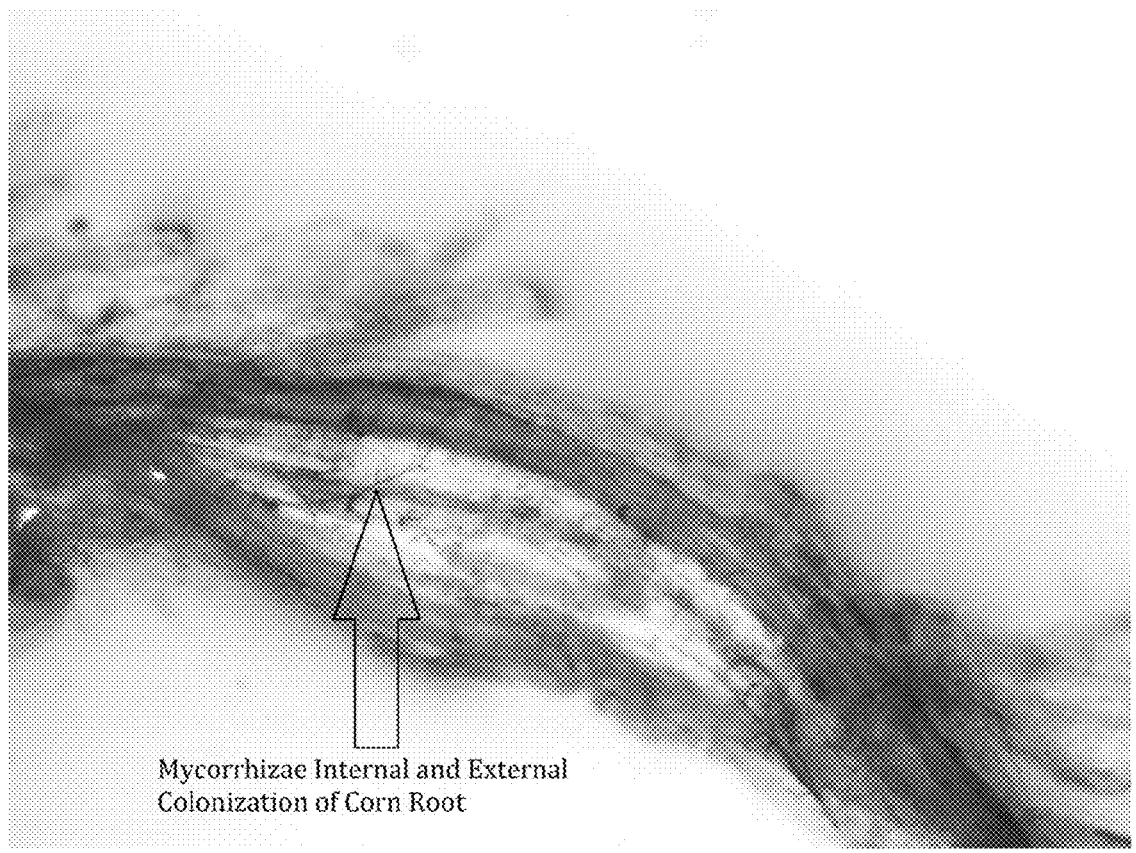
FIG. 4 is a photograph produced by staining with trypan blue a corn root embodying an embodiment of the invention.

Referring to FIG. 4, a photograph is presented that was produced by staining a corn root with trypan blue. The corn root was taken from a field where the treatment applied was Phytate+Mycorrhizae+*T. virens*+*B. amyloliquefaciens* and 3 gallons of 10-34-0 in furrow at planting. When the root sample was taken 18 days after emergence, the root was already showing healthy mycorrhizal colonization both outside and inside the root. The magnification of the root is 50 times (50x).

Figure 5:
FIG. 5 is a photograph of roots of a control corn plant (on the left) and a corn plant treated with an illustrative embodiment of the invention (on the right), respectively.

Referring to FIG. 5, a photograph is presented of the roots of corn plants that are 28 days old. This photograph provides empirical evidence that the illustrative embodiment of the invention used is effective in producing signals that cause Mycorrhizae propagules to germinate and colonize the root of corn in a high phosphorus environment. The increase in root proliferation is caused by mycorrhizae increasing root growth.

Figure 6:
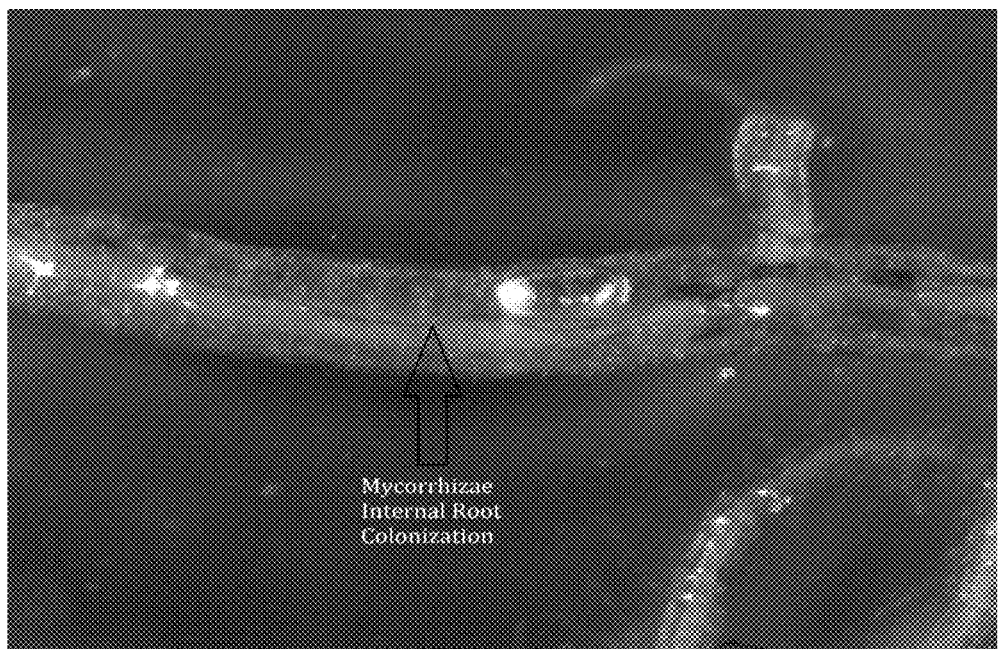
FIG. 6 is a photograph showing the mycorrhizal hyphae structure colonizing inside a root of a plant treated with an illustrative embodiment of the invention.

Referring to FIG. 6, a photograph is presented of a root with Mycorrhizae stained blue with trypan blue and photographed under a microscope at 50x magnification. This photograph shows the mycorrhizal hyphae structure colonizing inside the root.

Figure 7:
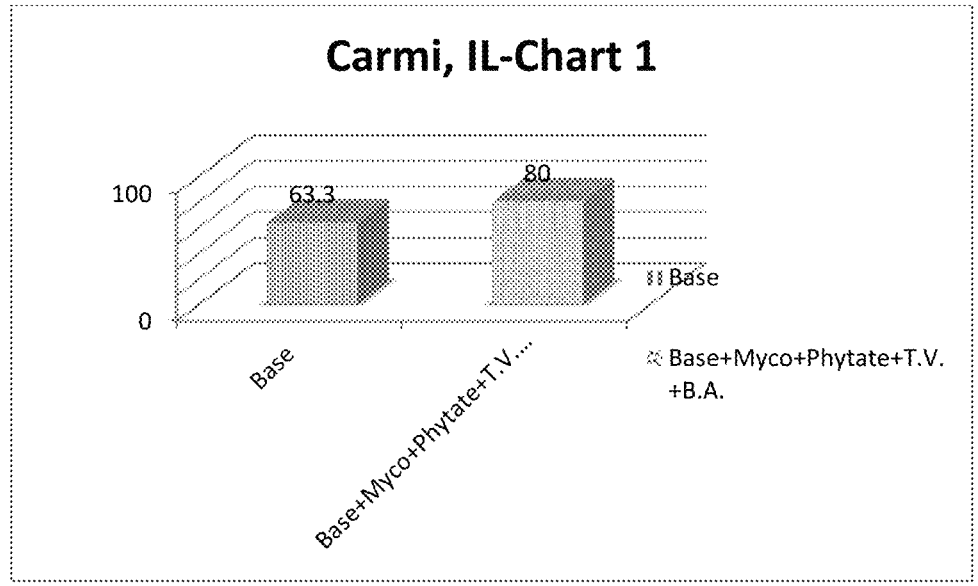
FIG. 7 is a chart that presents data that were collected at Carmi, Ill. with treatments on hybrid corn during the 2012 growing season.

Referring to FIG. 7, a chart is presented that shows data that were collected at Carmi, Ill. with treatments on hybrid corn during the 2012 growing season. The location was under significant drought pressure as indicated by the low yield. The yield of corn under average moisture conditions is expected to be 200+ bushels per acre in this area. These data show that the illustrative embodiment of the invention used was effective under very low moisture conditions. The location has a standard application of fertilizer for a 200+ bushel yield, which would provide a high phosphorus environment. Use of the illustrative embodiment of the invention clearly produced an improved yield response of 16+ bushels per acre that was provided by the Mycorrhizae root colonization in spite of the high phosphorus conditions. These data show the in-furrow application of Mycorrhizae+Phytate+*Trichoderma virens*+*Bacillus amyloliquefaciens* increased yield in this high phosphorus—low moisture environment. The treatments were as follows:

Base=Industry standard fungicide and insecticide seed treatment

Base+Myco+Phytate+T.V.+B.A.=Base seed treatment+an in-furrow application of 5 gallons of a solution containing 4 strains of Mychorrizae propagules at 30,000 propagules per acre+40% Phytate at 1 quart per acre+*Trichoderma virens* at 4.20E9 colony forming units per acre, *Bacillus amyloliquefaciens* at 8.40E10 colony forming units per acre.

Figure 8:
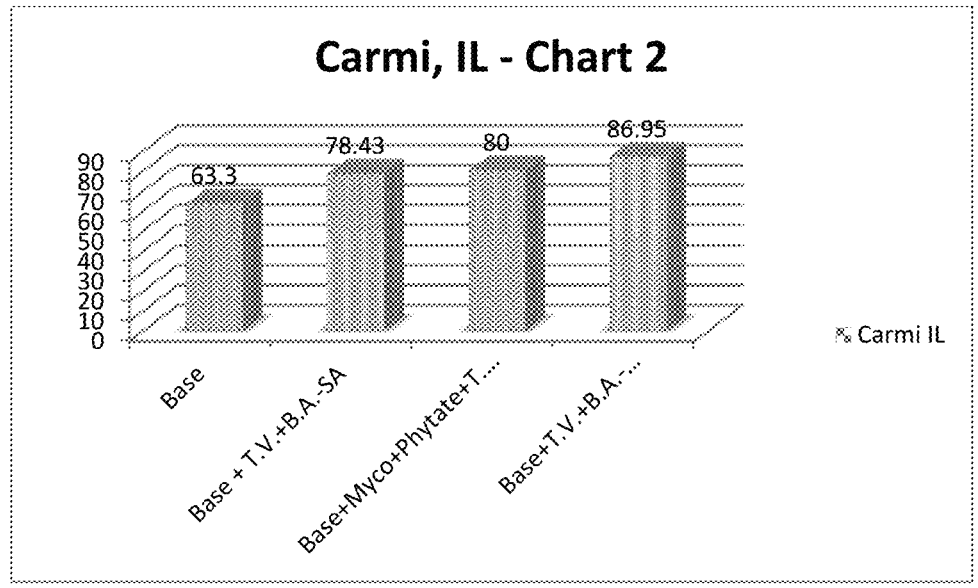
FIG. 8 is a chart that shows that the interaction of the components of an illustrative embodiment of the invention.

Referring to FIG. 8, more data from Carmi, Ill. are presented. This chart shows that the interaction of the components of the illustrative embodiment of the invention in an in-furrow application are not hindered by the *T. virens+B. amyloliquefaciens* active ingredients applied to the seed. In fact, the combined Seed Applied (SA) *T. virens+B. amyloliquefaciens* and the in furrow application of the invention resulting a 23+ bushel per acre yield advantage. The treatments were as follows:

Base=Industry standard fungicide and insecticide seed treatment

Base+T.V.+B.A.–SA=Base+*Trichoderma virens+Bacillus amyloliquefaciens* that is seed applied (SA).

Base+Myco+Phytate+T.V.+B.A.=Base seed treatment+an in-furrow application of 5 gallons of a solution containing 4 strains of Mychorrizae propagules at 30,000 propagules per acre+40% Phytate at 1 quart per acre+*Trichoderma virens* at 4.20E9 colony forming units per acre, *Bacillus amyloliquefaciens* at 8.40E10 colony forming units per acre.

Base+T.V+B.A–SA+Myco+Phytate+T.V+B.A.=Base+T.V.+B.A.(SA) plus an in-furrow application of 5 gallons of a solution containing 4 strains of Mychorrizae propagules at 30,000 propagules per acre+40% Phytate at 1 quart per acre+*Trichoderma virens* at 4.20E9 colony forming units per acre, *Bacillus amyloliquefaciens* at 8.40E10 colony forming units per acre.

Figure 9:
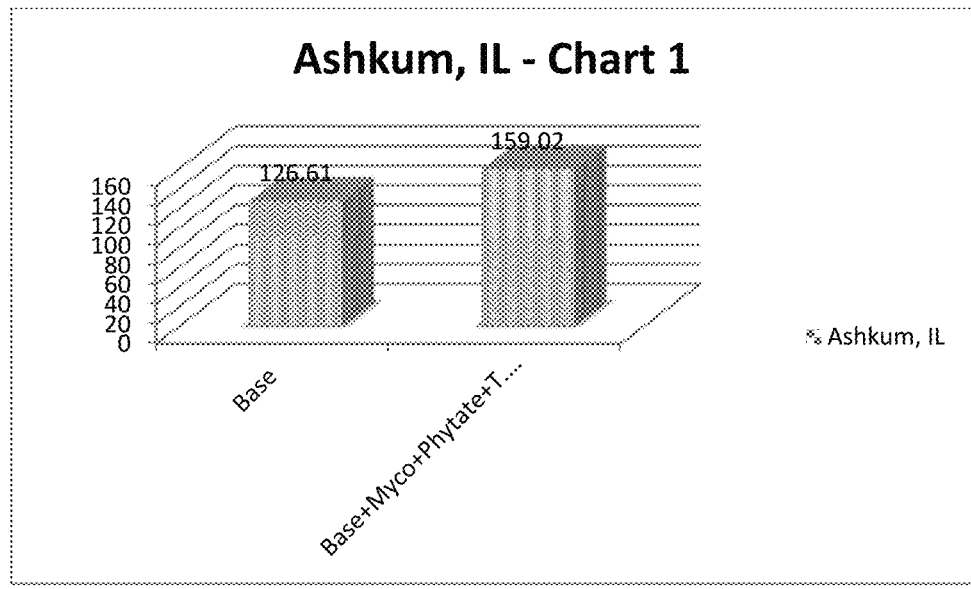
FIG. 9 is a chart that presents data that were collected at Ashkum, Ill. with treatments on hybrid corn during the 2012 growing season.

Referring to FIG. 9, a chart is presented that shows data collected at Ashkum, Ill. with treatments on hybrid corn during the 2012 growing season. The location was under significant drought pressure as indicated by the low yield, however, drought pressure was not a great as at the Carmi Ill. location. The yield of corn under average moisture conditions is expected to be 200+ bushels per acre in this area. These data show that the illustrative embodiment of the invention used is effective under very low moisture conditions. The location has a standard application of fertilizer for a 200+ bushel yield, which would provide a high phosphorus environment. The data clearly show the improved yield response of 32+ bushels per acre provided by the Mycorrhizae root colonization as a result of use of an illustrative embodiment of the invention in spite of the high phosphorus conditions. The data confirm in-furrow application of Mycorrhizae+Phytate+*Trichoderma virens*+*Bacillus amyloliquefaciens* increased yield in this high phosphorus—low to medium moisture environment. The treatments were as follows:

Base=Industry standard fungicide and insecticide seed treatment

Base+Myco+Phytate+T.V.+B.A.=Base seed treatment+an in-furrow application of 5 gallons of a solution containing 4 strains of Mychorrizae propagules at 30,000 propagules per acre+40% Phytate at 1 quart+*Trichoderma virens* at 4.20E9 colony forming units per acre, *Bacillus amyloliquefaciens* at 8.40E10 colony forming units per acre.

Figure 10:
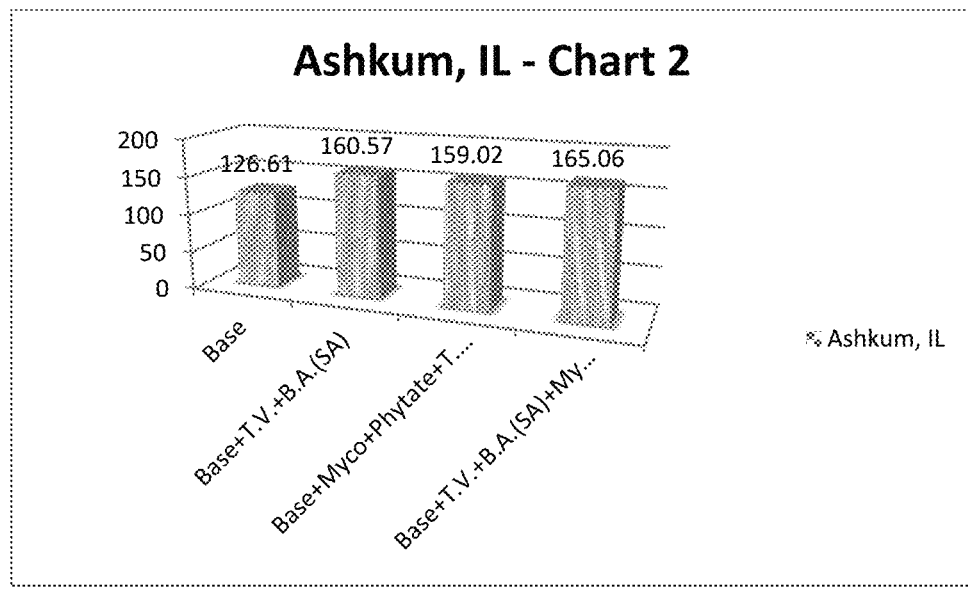
FIG. 10 is another chart that shows that the interaction of the components of an illustrative embodiment of the invention.

Referring to FIG. 10, data obtained at Ashkum, Ill. are presented. The chart shows that the interaction of the components of an illustrative embodiment of the invention in an in-furrow application are not hindered by the *T. virens+B. amyloliquefaciens* active ingredients applied to the seed. In fact, the combined Seed Applied (SA) *T. virens+B. amyloliquefaciens* and the in furrow application of the invention resulting a 38+ bushel per acre yield advantage. The treatments were as follows:

Base=Industry standard fungicide and insecticide seed treatment

Base+T.V.+B.A.–SA=Base+*Trichoderma virens+Bacillus amyloliquefaciens* that is seed applied (SA).

Base+Myco+Phytate+T.V.+B.A.=Base seed treatment+an in-furrow application of 5 gallons of a solution containing 4 strains of Mychorrizae propagules at 30,000 propagules per acre+40% Phytate at 1 quart per acre+*Trichoderma virens* at 4.20E9 colony forming units per acre, *Bacillus amyloliquefaciens* at 8.40E10 colony forming units per acre.

Base+T.V+B.A–SA+Myco+Phytate+T.V+B.A.=Base+T.V.+B.A.(SA) plus an in-furrow application of 5 gallons of a solution containing 4 strains of Mychorrizae propagules at 30,000 propagules per acre+40% Phytate at 1 quart per acre+*Trichoderma virens* at 4.20E9 colony forming units per acre, *Bacillus amyloliquefaciens* at 8.40E10 colony forming units per acre.

Figure 11:
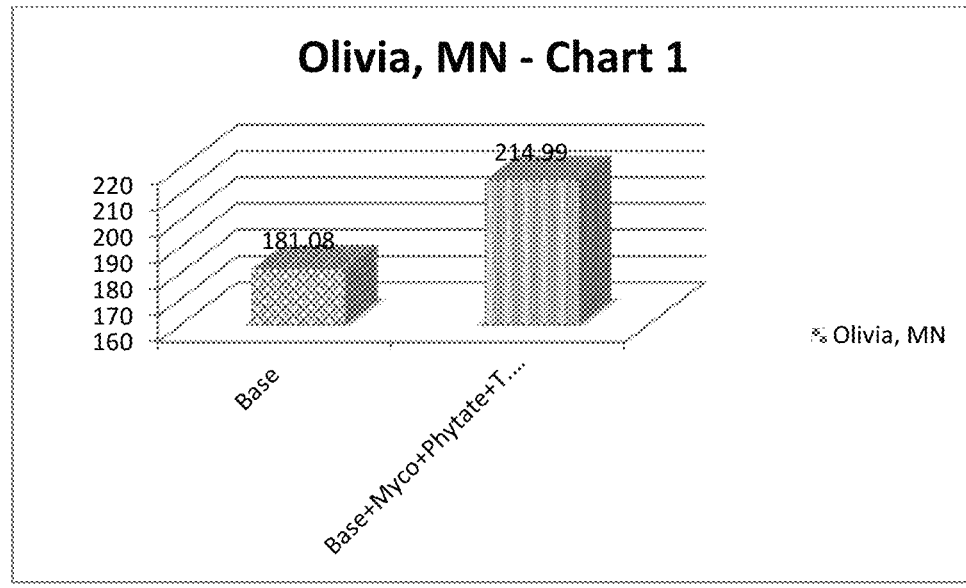
FIG. 11 is a chart that presents data that were collected at Olivia, Minn. with treatments on hybrid corn during the 2012 growing season.

Referring to FIG. 11, a chart is presented that shows data collected at Olivia, Minn. with treatments on hybrid corn during the 2012 growing season. This location had normal precipitation unlike the locations at Carmi and Ashkum, Ill. The yield of corn under average moisture conditions are expected to be 200+ bushels per acre in this area. These data show that the illustrative embodiment of the invention used is effective under adequate or normal moisture conditions. The location has a standard application of fertilizer for a 200+ bushel yield, which would provide a high phosphorus environment. Use of the illustrative embodiment of the invention clearly produced an improved yield response of 33+ bushels per acre provided by the Mycorrhizae root colonization in spite of the high phosphorus conditions. The data show the in-furrow application of Mycorrhizae+Phytate+*Trichoderma virens*+*Bacillus amyloliquefaciens* increased yield in this high phosphorus—adequate moisture environment. The treatments were as follows:

Base=Industry standard fungicide and insecticide seed treatment

Base+Myco+Phytate+T.V.+B.A.=Base seed treatment+an in-furrow application of 5 gallons of a solution containing 4 strains of Mychorrizae propagules at 30,000 propagules per acre+40% Phytate at 1 quart per acre+*Trichoderma virens* at 4.20E9 colony forming units per acre, *Bacillus amyloliquefaciens* at 8.40E10 colony forming units per acre.

Figure 12:
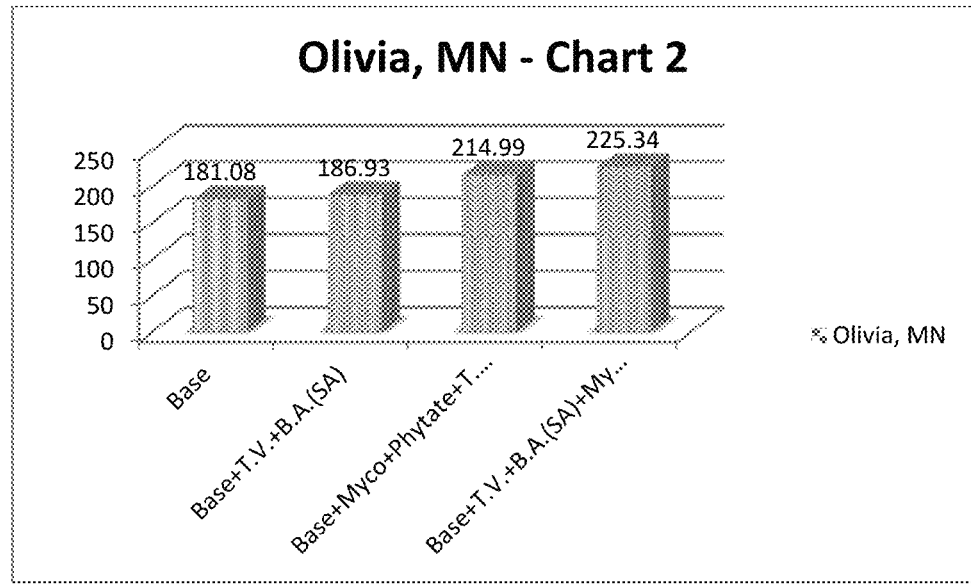
FIG. 12 is another chart that shows that the interaction of the components of an illustrative embodiment of the invention.

Referring to FIG. 12, a chart is presented that shows data from Olivia, Minn. The chart shows that the interaction of the components of the illustrative embodiment of the invention used in an in-furrow application are not hindered by the *T. virens+B. amyloliquefaciens* active ingredients applied to the seed. In fact, the combined Seed Applied (SA) *T. virens+B. amyloliquefaciens* and the in furrow application of the invention resulting a 44+ bushel per acre yield advantage. The treatments were as follows:

Base=Industry standard fungicide and insecticide seed treatment

Base+T.V.+B.A.−SA=Base+*Trichoderma virens+Bacillus amyloliquefaciens* that is seed applied (SA).

Base+Myco+Phytate+T.V.+B.A.=Base seed treatment+an in-furrow application of 5 gallons of a solution containing 4 strains of Mychorrizae propagules at 30,000 propagules per acre+40% Phytate at 1 quart per acre+*Trichoderma virens* at 4.20E9 colony forming units per acre, *Bacillus amyloliquefaciens* at 8.40E10 colony forming units per acre.

Base+T.V+B.A−SA+Myco+Phytate+T.V+B.A.=Base+T.V.+B.A.(SA) plus an in-furrow application of 5 gallons of a solution containing 4 strains of Mychorrizae propagules at 30,000 propagules per acre+40% Phytate at 1 quart+*Trichoderma virens* at 4.20E9 colony forming units per acre, *Bacillus amyloliquefaciens* at 8.40E10 colony forming units per acre.

Figure 13:
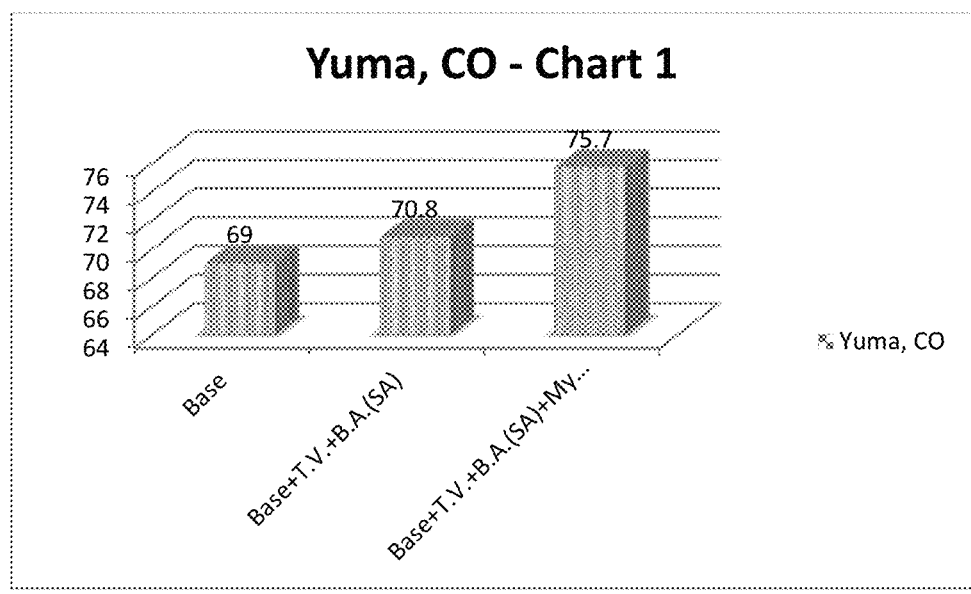
FIG. 13 is a chart presenting yield data on soybeans that were grown in a field trial at the Irrigation Research Foundation, Yuma, Colo. in the growing season 2012.

Referring to FIG. 13, a chart is presented that shows yield data on soybeans that were grown in a field trial at the Irrigation Research Foundation, Yuma, Colo. in the growing season 2012. At this trial location, the soybeans were irrigated and a fertilizer with the analysis of 15-20-0-2s-.027ZN was applied in furrow at a rate of 4.5 gallons per acre. The data again confirm that an illustrative embodiment of the invention performs in a similar manner on a dicot legume, in this case soybeans, just as it does on a monocot, corn in the presence of high phosphorus. The data also confirm that the use of a seed applied (SA) *T. virens+B. amyloliquefaciens* continued to allow the embodiment of the invention used to produce increased yield. The overall increase of the combined treatments was 6.7 bushel of soybeans per acre. The treatments were as follows:

Base=Industry standard fungicide and insecticide seed treatment

Base+T.V.+B.A.−SA=Base+*Trichoderma virens+Bacillus amyloliquefaciens* that is seed applied (SA).

Base+T.V+B.A−SA+Myco+Phytate+T.V+B.A.=Base+T.V.+B.A.(SA) plus an in-furrow application of 5 gallons of a solution containing 4 strains of Mychorrizae propagules at 30,000 propagules per acre+40% Phytate at 1 quart per acre+*Trichoderma virens* at 4.20E9 colony forming units per acre, *Bacillus amyloliquefaciens* at 8.40E10 colony forming units per acre.

Many variations of the invention will occur to those skilled in the art. Some variations include liquid formulations. Other variations call for solid formulations. All such variations are intended to be within the scope and spirit of the invention.

Although some embodiments are shown to include certain features or steps, the applicant specifically contemplates that any feature or step disclosed herein may be used together or in combination with any other feature or step in any embodiment of the invention. It is also contemplated that any feature or step may be specifically excluded from any embodiment of the invention.

The invention claimed is:

1. A composition, comprising:
    a *Trichoderma virens* component comprising *Trichoderma virens* G1-3;
    a *Bacillus amyloliquefaciens* component;
    a mycorrhizal fungus or mycorrhizal fungi component; and
    a phytate or phytic acid component.

2. The composition of claim 1, wherein said *Trichoderma virens* component comprises about $1 \times 10^{11}$ to about $1 \times 10^7$ colony forming units per gram of *Trichoderma virens* G1-3.

3. The composition of claim 1, wherein said *Trichoderma virens* component comprises about $4.2 \times 10^9$ to about $6.75 \times 10^8$ colony forming units per gram of *Trichoderma virens* G1-3.

4. The composition of claim 1, wherein said *Trichoderma virens* component comprises about $5 \times 10^8$ colony forming units per gram of *Trichoderma virens* G1-3.

5. The composition of claim 1, wherein said *Bacillus amyloliquefaciens* component comprises about $5 \times 10^{11}$ to about $1 \times 10^7$ colony forming units per gram of *Bacillus amyloliquefaciens* TJ1000.

6. The composition of claim 1, wherein said *Bacillus amyloliquefaciens* component comprises about $1.35 \times 10^{10}$ to about $8.40 \times 10^{10}$ colony forming units per gram of *Bacillus amyloliquefaciens* TJ1000.

7. The composition of claim 1, wherein said *Bacillus amyloliquefaciens* component comprises about $5 \times 10^{11}$ to about $1 \times 10^7$ colony forming units per gram of *Bacillus amyloliquefaciens* FZB24.

8. The composition of claim 1, wherein said *Bacillus amyloliquefaciens* component comprises about $1.35 \times 10^{10}$ to about $8.40 \times 10^{10}$ colony forming units per gram of *Bacillus amyloliquefaciens* FZB24.

9. A method, comprising applying the composition of claim 1 to a soil.

10. The method of claim 9, wherein the composition of claim 1 is applied to the soil at a rate of about 1.35 grams per acre.

11. A composition, comprising:
    a *Trichoderma virens* component comprising *Trichoderma virens* G1-21;
    a *Bacillus amyloliquefaciens* component;
    a mycorrhizal fungus or mycorrhizal fungi component; and
    a phytate or phytic acid component.

12. The composition of claim 11, wherein said *Trichoderma virens* component comprises about $1 \times 10^{11}$ to about $1 \times 10^7$ colony forming units per gram of *Trichoderma virens* G1-21.

13. The composition of claim 11, wherein said *Trichoderma virens* component comprises about $4.2 \times 10^9$ to about $6.75 \times 10^8$ colony forming units per gram of *Trichoderma virens* G1-21.

14. The composition of claim 11, wherein said *Trichoderma virens* component comprises about $5 \times 10^8$ colony forming units per gram of *Trichoderma virens* G1-21.

15. The composition of claim 11, wherein said *Bacillus amyloliquefaciens* component comprises about $5 \times 10^{11}$ to about $1 \times 10^7$ colony forming units per gram of *Bacillus amyloliquefaciens* TJ1000.

16. The composition of claim 11, wherein said *Bacillus amyloliquefaciens* component comprises about $1.35 \times 10^{10}$ to about $8.40 \times 10^{10}$ colony forming units per gram of *Bacillus amyloliquefaciens* TJ1000.

17. The composition of claim 11, wherein said *Bacillus amyloliquefaciens* component comprises about $5 \times 10^{11}$ to about $1 \times 10^7$ colony forming units per gram of *Bacillus amyloliquefaciens* FZB24.

18. The composition of claim 11, wherein said *Bacillus amyloliquefaciens* component comprises about $1.35 \times 10^{10}$ to about $8.40 \times 10^{10}$ colony forming units per gram of *Bacillus amyloliquefaciens* FZB24.

19. A method, comprising applying the composition of claim 11 to a soil.

20. The method of claim 19, wherein the composition of claim 11 is applied to the soil at a rate of about 1.35 grams per acre.

* * * * *